United States Patent
Chen et al.

(12) 
(10) Patent No.: US 6,638,760 B1
(45) Date of Patent: Oct. 28, 2003

(54) METHOD AND APPARATUS FOR FLOW-THROUGH HYBRIDIZATION

(75) Inventors: Jer-Kang Chen, Palo Alto, CA (US); Claudia Chiesa, Redwood City, CA (US); George A. Fry, San Carlos, CA (US); Vergine C. Furniss, San Mateo, CA (US); Stephen M. Lambert, Castro Valley, CA (US); Roger O'Neill, San Carlos, CA (US); Majid Mehrpouyan, San Jose, CA (US)

(73) Assignee: PE Corporation (NY), Norwalk, CO (US)

( * ) Notice: Subject to any disclaimer, the term of this patent is extended or adjusted under 35 U.S.C. 154(b) by 0 days.

(21) Appl. No.: 09/204,865

(22) Filed: Dec. 3, 1998

Related U.S. Application Data

(60) Provisional application No. 60/135,516, filed on Nov. 25, 1998.

(51) Int. Cl.[7] .............................. C12M 1/34; C12Q 1/68; C12P 19/34; C07H 21/02; C07H 21/04

(52) U.S. Cl. ................. 435/287.2; 436/6; 436/91.1; 436/287.1; 536/23.1; 536/24.3; 536/24.33

(58) Field of Search .......................... 435/6, 91.1, 91.2, 435/93.5, 283.1, 287.1, 183, 287.2; 436/177, 807, 94; 536/24.3, 23.1, 24.33, 25.3

(56) References Cited

U.S. PATENT DOCUMENTS

| | | | |
|---|---|---|---|
| 4,366,241 A | | 12/1982 | Tom et al. ..................... 435/7 |
| 4,632,901 A | | 12/1986 | Valkirs et al. ................. 435/5 |
| 4,727,019 A | | 2/1988 | Valkirs et al. ................. 435/5 |
| 4,787,963 A | * | 11/1988 | MacConnell ............ 204/180.1 |
| 4,818,677 A | | 4/1989 | Hay-Kaufman et al. ....... 435/4 |
| 5,369,012 A | | 11/1994 | Koontz et al. ............. 435/7.92 |
| 5,667,976 A | * | 9/1997 | Van Ness et al. ............... 435/6 |
| 5,700,559 A | | 12/1997 | Sheu et al. .............. 428/319.7 |
| 5,723,219 A | | 3/1998 | Kolluri et al. .......... 428/411.1 |
| 5,741,647 A | * | 4/1998 | Tam .............................. 435/6 |
| 5,804,384 A | | 9/1998 | Müller et al. ................... 435/6 |
| 5,843,662 A | * | 12/1998 | Dean et al. ..................... 435/6 |
| 5,843,767 A | * | 12/1998 | Beattie .................... 435/287.1 |
| 6,060,240 A | * | 5/2000 | Kamb et al. ................... 435/6 |

FOREIGN PATENT DOCUMENTS

| | | | |
|---|---|---|---|
| CA | 1110511 | * | 11/1980 |
| EP | 0455905 A2 | * | 11/1991 |
| EP | 0 605 828 A1 | | 7/1994 |
| US | 0455905 A2 | * | 11/1991 |
| US | 0605828 A1 | * | 7/1994 |
| WO | WO 95/18851 A1 | | 7/1995 |

OTHER PUBLICATIONS

Bio–Rad Catalog, p. 71, 1998/99. Published by Bio–Rad Laboratories, 2000 Alfred Nobel Drive, Hercules, CA 94547, 1998/1999.*

Fahy et al., Design and synthesis of polyacrylamide–based oligonucleotide supports for use in nucleic acid diagnostics. Nucleic Acids Res. 21, 1819–1826, 1993.*

Bannwarth, et al.; "Formation of Carboxamides with N, N, N', N'–Tetramethyl (Succinimido) Uronium Tetrafluoroborate in Aqueous/Organic Solvent Systems"; Tetrahedron Letters, vol. 32, No. 9, pp. 1157–1160; 1991.

Bannwarth, et al.; "Bathophenanthroline–ruthenium(II) complexes as Non–Radioactive Labels for Oligonucleotides which Can Be Measured by Time–Resolved Fluorescence Techniques"; Helvetica Chimica Acta, vol. 71, pp. 2085–2099; 1988.

Bath, et al.; "Imaging Molecular in Porous Membranes. Observation and Analysis of Electroosmotic Flow in Individual Pores Using the Scanning Electrochemical Microscope"; Anal. Chem, vol. 70, pp. 1047–1058; 1998.

Chan, et al.; "The Biophysics of DNA Hybridization with Immobilized Oligonucleotide Probes"; Biophysical Journal, vol. 69, pp. 2243–2255; Dec. 1995.

Chan, et al.; "Adsorption and Surface Diffusion of DNA Oligonucleotides at Liquid/Solid Interfaces"; Langmuir, vol. 13, pp. 320–329; 1997.

Cohen, et al.; "Covalent Attachment of DNA Oligonucleotides to Glass"; Oxford University Press, pp. 911–912; Jan. 1997.

Dubiley, et al.; "Fractionation, Phosphorylation and Ligation of Oligonucleotide Microchips to Enhance Sequencing by Hybridization"; Nucleic Acids Research, vol. 25, No. 12, pp. 2259–2265; May 1997.

Edman, et al.; "Electric Field Directed Nucleic Acid Hybridization on Microchips"; Nucleic Acids Research, vol. 25, No. 24, pp. 4907–4914; Nov. 1997.

Fahy, et al.; "Design and Synthesis of Polyacrylamide–based Oligonucleotide Supports for Use in Nucleic Acid Diagnostics"; Nucleic Acids Research, vol. 21, No. 8, pp. 1819–1826; Mar. 1993.

Finson, et al.; "Surface Treatment"; The Wiley Encyclopedia of Packaging Technology, Second Edition, pp. 867–874; 1997.

Fotin, et al.; "Parallel Thermodynamic Analysis of Duplexes on Oligodeoxyribonucleotide Microchips"; Nucleic Acids Research, vol. 26, No. 6, pp. 1515–1521; Feb. 1998.

Kato, et al.; "Immobilization of DNA onto a Polymer Support and Its Potentiality as Immunoadsorbant"; Biotechnology and Bioengineering, vol. 51, pp. 581–590; 1996.

(List continued on next page.)

Primary Examiner—Ethan Whisenant
Assistant Examiner—Frank Lu
(74) Attorney, Agent, or Firm—Pennie & Edmonds LLP

(57) ABSTRACT

The present invention provides substrates and apparatuses for efficient, rapid and specific capture, and optimal recovery, of nucleic acids, as well as methods of their use. The substrate is porous in nature and has a capture polynucleotide capable of hybridizing to a target nucleic acid immobilized thereon. Upon flowing a sample containing or suspected of containing the target nucleic acid through the porous substrate, the target nucleic acid is rapidly captured. Following capture, the target nucleic acid can be efficiently recovered for subsequent use.

45 Claims, 6 Drawing Sheets

OTHER PUBLICATIONS

Knorr, et al.; "New Coupling Reagents in Peptide Chemistry"; Tetrahedron Letters, vol. 30, No. 15, pp. 1927–1930; 1989.

Lamture, et al.; "Direct Detection of Nucleic Acid Hybridization on the Surface of a Charge Coupled Device"; Nucleic Acids Research, vol. 22, No. 11, pp. 2121–2125; Mar. 1994.

Nancy B. Mateo; "Using Gas Plasma to Reengineer Surfaces"; Medical Product Manufacturing News, 2 pages; Sep./Oct. 1990.

Narayanaswami, et al.; "Detection of Oligonucleotides Hybridized to a Planar Surface Using Matrix–Assisted Laser–Desorption Mass Spectroscopy"; J. Am. Chem. Soc., vol. 119, No. 29, pp. 6888–6890; Jul. 1997.

O'Donnell, et al.; "High–Density, Covalent Attachment of DNA to Silicon Wafers for Analysis by MALDI–TOF Mass Spectrometry"; Anal. Chem., vol. 69, pp. 2438–2443; 1997.

Parik, et al.; "A Manifold Support for Molecular Genetic Reactions"; Analytical Biochemistry, vol. 211, pp. 144–150; 1993.

S. E. Rasmussen; "Covalent Immobilization of Biomolecules onto Polystyrene MicroWells for Use in Biospecific Assays"; First Congress on Advanced Concept in Biology, Paris; Dec. 5–8, 1989.

Saiki, et al.; "Genetic Analysis of Amplified DNA with Immobilized Sequence–Specific Oligonucleotide Probes"; Proc. Natl. Acad. Sci. USA, vol. 86, pp. 6230–6234; Aug. 1989.

Sera–Mag™ Streptavidin Magnetic Microparticles, Particle Technology, pp. 1–7, Nov. 1996.

Sosnowski, et al.; "Rapid determination of Single Base Mismatch Mutations in DNA Hybrids by Direct Electric Field Control"; Proc. Natl. Acad. Sci. USA, vol. 94, pp. 1119–1123; Feb. 1997.

Vesnaver, et al.; "The Contribution of DNA Single–Stranded Order to the Thermodynamics of Duplex Formation"; Proc. Natl. Acad. Sci. USA, vol. 88, pp. 3569–3573; May 1991.

Wilchek, et al.; "Improved Method for Preparing N–Hydroxysuccinimide Ester–Containing Polymers for Affinity Chromatography"; Bioconjugate Chem., vol. 5, pp. 491–492; 1994.

Wolf, et al.; "Rapid Hybridization Kinetics of DNA Attached to Submicron Latex Particles;" Nucleic Acids Research, vol. 15, No. 7, pp. 2911–2926; 1987.

Bio–Rad Laboratories. Life Science Research Products. Bio–Rad Catalog. 1993, pp. 17–18.

Cheng et al., 1996, "Chip PCR. II. Investigation of different PCT amplification systems in microfabricated silicon–glass chips," *Nucleic Acids Res.* 24:380–386.

Chou et al., 1996, "Affinity methods for purification of DNA sequencing reaction products for mass spectrometric analysis," *Rapid Commun. Mass. Spect.* 10:1410–1414.

* cited by examiner

FORWARD SEQUENCING PRIMER:

5'-CACTCACGCAAACGG-linker-TGTAAAACGACGGCCAGT-3'

Capture complement            Sequencing primer

REVERSE SEQUENCING PRIMER:

5'-AACTCTCCCAAGAGCAC-linker-CAGGAAACAGCTATGACC-3'

Capture complement            Sequencing primer

Figure 1:
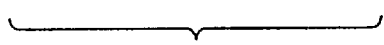
Figure 1:
Figure 1:
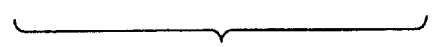
Figure 1:
Figure 1:
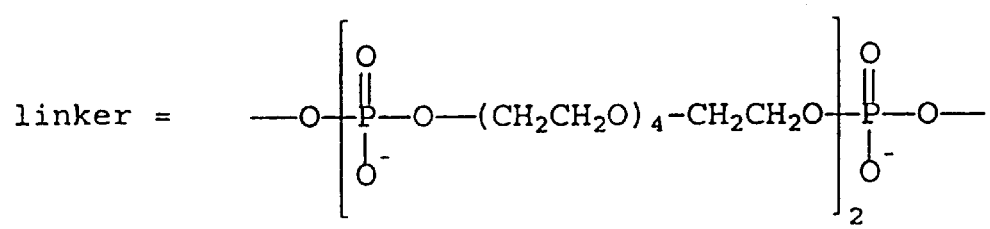

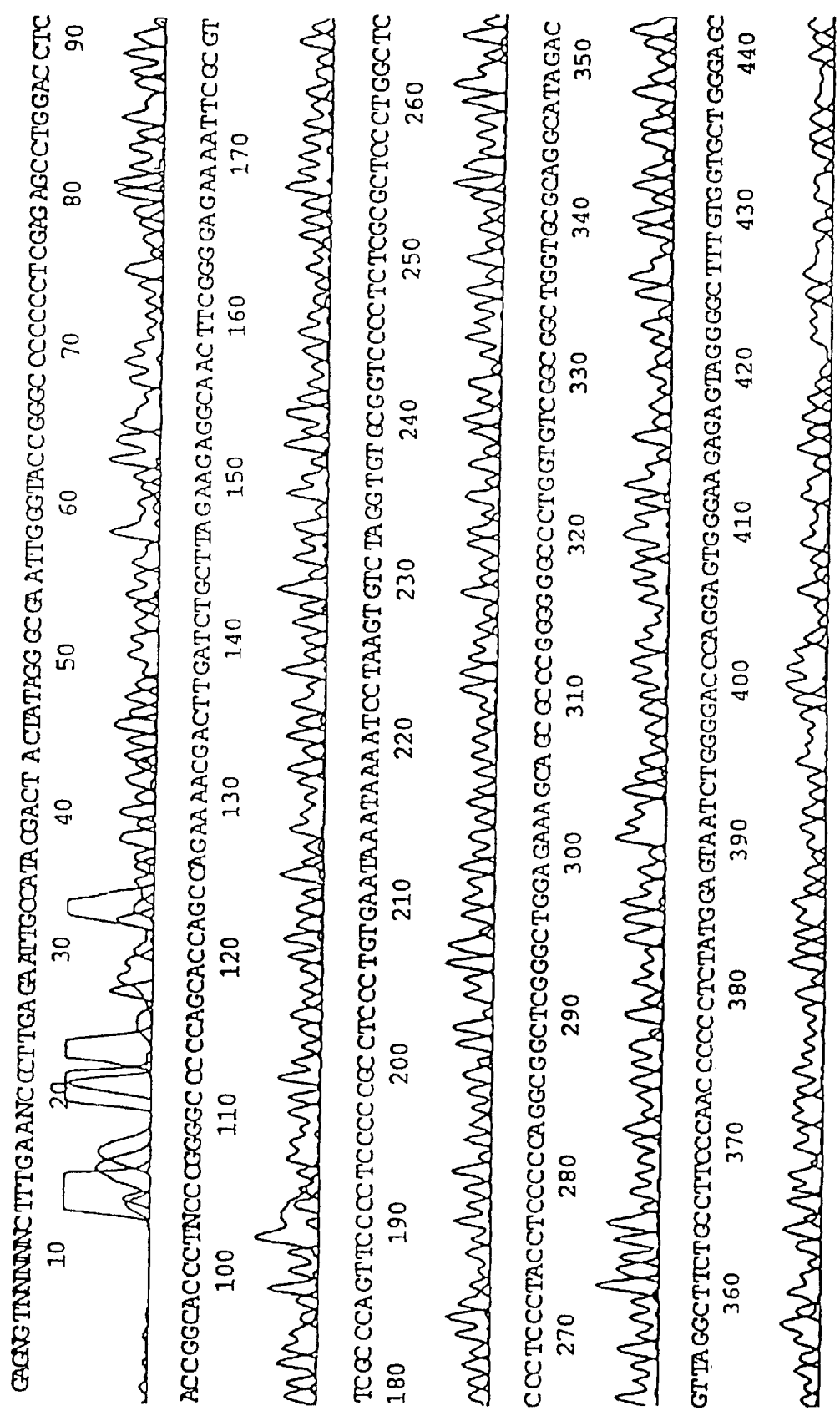
FIG. 2A1

CGAGGAAGAAATGAAATGTGCAGTTGAGTGTGTTGCTCGCATCCCAGGGAGCAAATGCAGTGCTGATTGTCTGTTGCTGAGATAGCCTTTTGT
450         460         470         480         490         500         510         520         530

TCGGAACATAAGGTTTAAGAAACACACACACGTTTTCTGGGGTCTCTTGTTAGATGTAAATGTGCGGATCCAGACCCTTACTATGCAGTGTA
540         550         560         570         580         590         600         610         620

AGCTCAATTGGGTTACTAATCACCCCGCCCACCCCCAAACAATGGATATATTTGAAATGGAACCTCATTCAACTTCTAGGCTGAGAGTA
630         640         650         660         670         680         690         700         710

TTGCCTTCAACCTATTTCATTCTAGACTAAGCAACCATTCAACTGAGATAATAAAGCAAACAATAACCNTTGATCATGATGTCTACCAAAAA
720         730         740         750         760         770         780         790         800

ATGTGCCCCGGAAAGTTCTTTAGGAATTGTAATGAGAAANAAAATGAAAATGGGCATAAATTCTTTT
810         820         830         840         850         860         870

FIG. 2A2

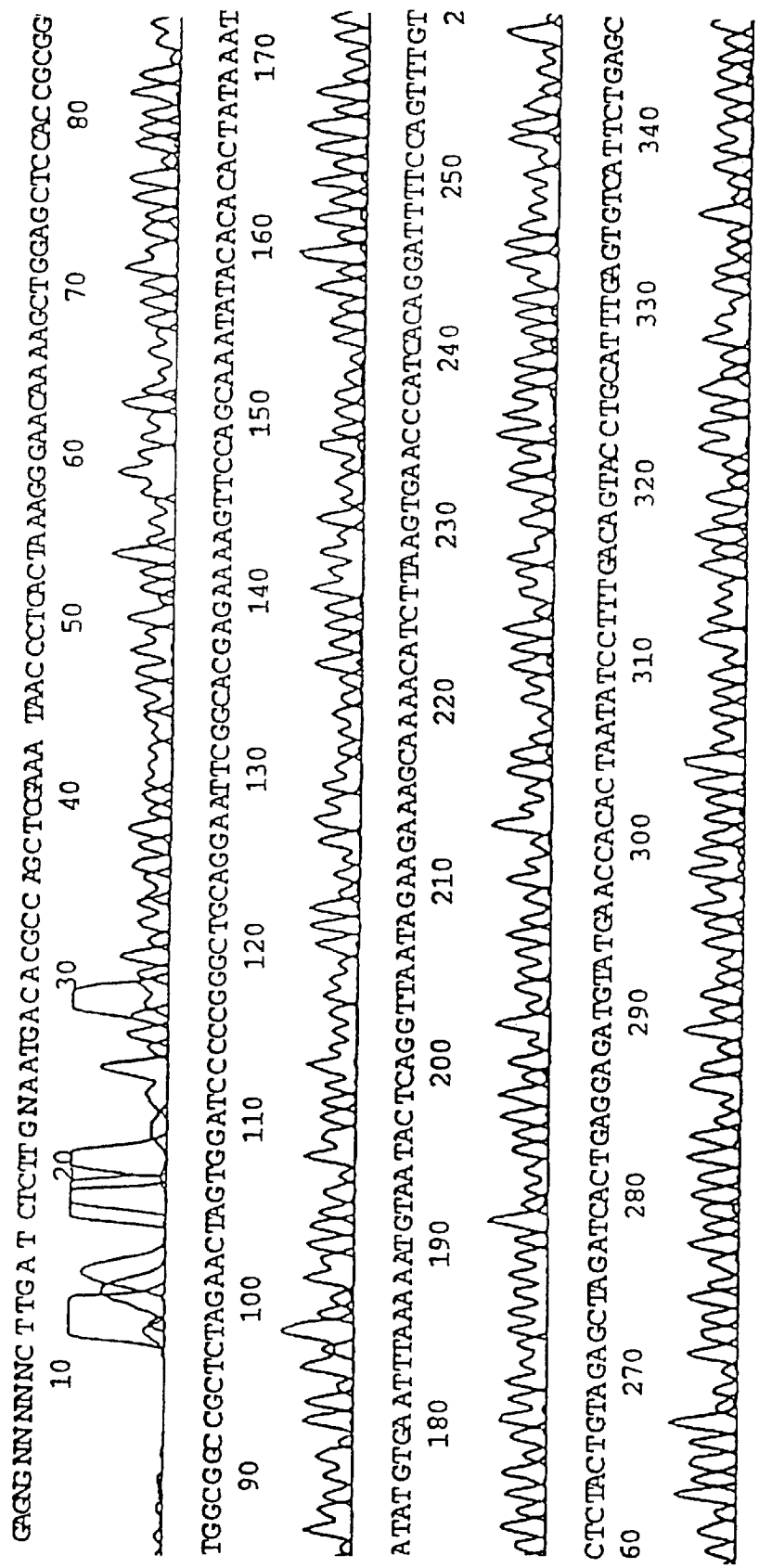
FIG. 2B1

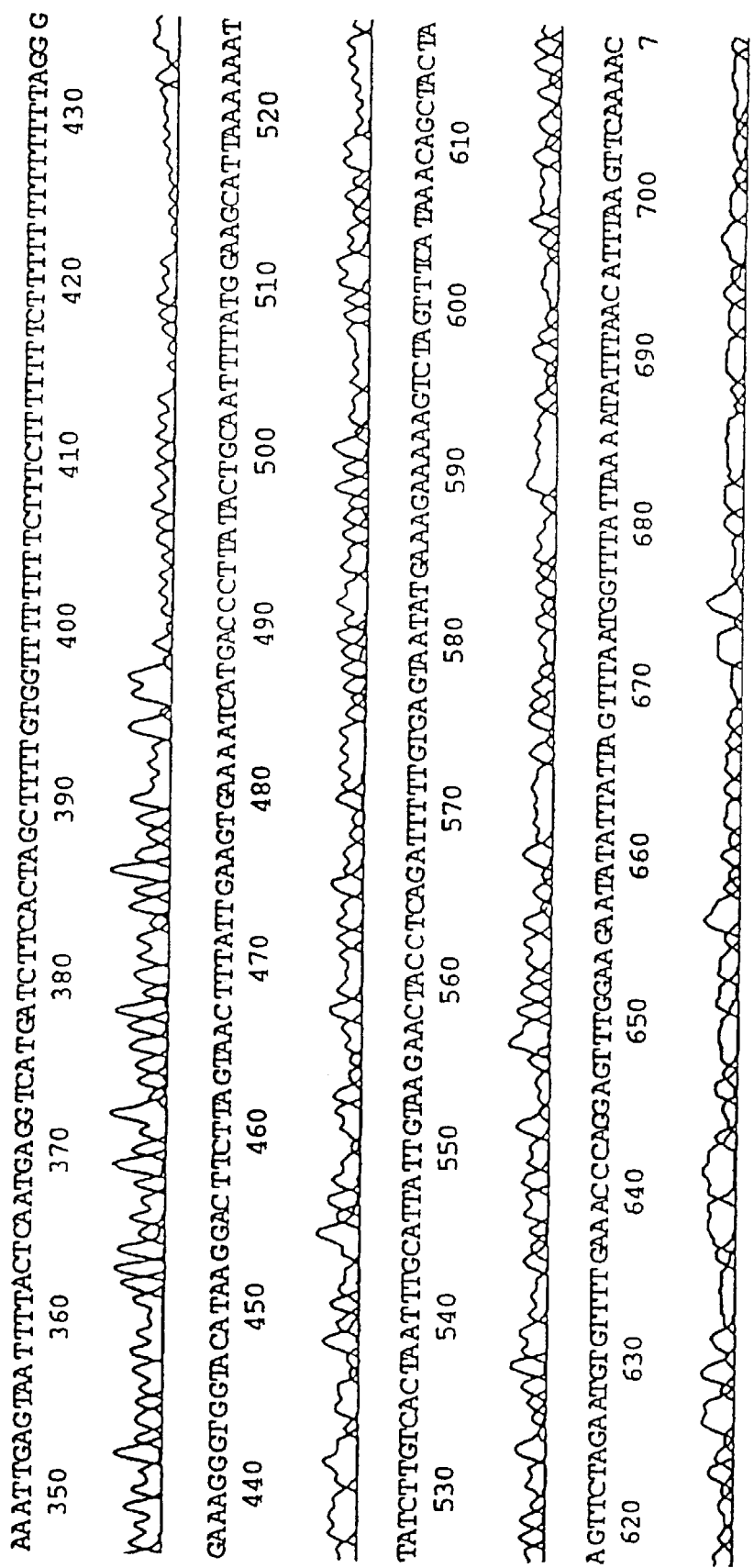
FIG. 2B2

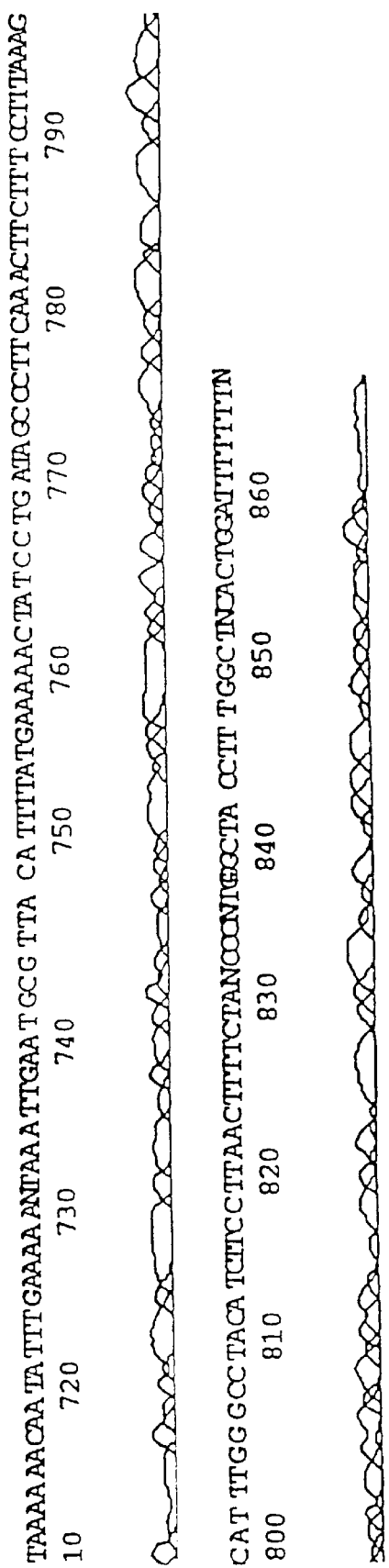
FIG. 2B3

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Capture polynucleotide
<220> FEATURE:
<221> NAME/KEY: modified_base
<222> LOCATION: 15
<223> OTHER INFORMATION: n = Guanine modified at the 3'-terminus with
      (pentaethyleneglycol)2-(CH2)6-NH2

<400> SEQUENCE: 1
ccgtttgcgt gagtn                                                    15

<210> SEQ ID NO 2
<211> LENGTH: 17
<212> TYPE: DNA
<213> ORGANISM: Artificial Sequence
<220> FEATURE:
<223> OTHER INFORMATION: Capture polynucleotide
<220> FEATURE:
<221> NAME/KEY: modified_base
<222> LOCATION: 17
<223> OTHER INFORMATION: n = Thymine modified at the 3'-terminus with
      (pentaethyleneglycol)2-(CH2)6-NH2

<400> SEQUENCE: 2
gtgctcttgg gagagtn                                                  17

<210> SEQ ID NO 3
<211> LENGTH: 15
<212> TYPE: DNA
<213> ORGANISM: Artificial Sequence
<220> FEATURE:
<223> OTHER INFORMATION: Capture complement

<400> SEQUENCE: 3
cactcacgca aacgg                                                    15

<210> SEQ ID NO 4
<211> LENGTH: 18
<212> TYPE: DNA
<213> ORGANISM: Artificial Sequence
<220> FEATURE:
<223> OTHER INFORMATION: Sequencing Primer

<400> SEQUENCE: 4
tgtaaaacga cggccagt                                                 18

<210> SEQ ID NO 5
<211> LENGTH: 17
<212> TYPE: DNA
<213> ORGANISM: Artificial Sequence
<220> FEATURE:
<223> OTHER INFORMATION: Capture complement

<400> SEQUENCE: 5
```

-continued aactctccca agagcac                                                    17

<210> SEQ ID NO 6
<211> LENGTH: 18
<212> TYPE: DNA
<213> ORGANISM: Artificial Sequence
<220> FEATURE:
<223> OTHER INFORMATION: Sequencing primer

<400> SEQUENCE: 6
caggaaacag ctatgacc                                                   18

<210> SEQ ID NO 7
<211> LENGTH: 877
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(877)
<223> OTHER INFORMATION: n = A,T,C or G

<400> SEQUENCE: 7
gagngtnnnn nctttgaanc ccttgagaat tgccatacga ctactatagg gcgaattggg      60
taccgggccc ccctcgaga gcctggacct caccggcacc ctncccgggg cccccagcac      120
cagccagaaa acgacttgat ctgcttagaa gaggcaactt cggggagaaa attcgcgttc     180
gcccagttcc cctccccgc ctccctgtga ataaataaaa tcctaagtgt ctaggtgtgc      240
ggtcccctct cgcgctccct ggctcccctc cctacctccc caggcggct cgggctggag      300 aaagcagcgc ccgggggggcc ctggtgtcgg cggctggtgc gcaggcatag acgttaggct    360
tctgccttcc caacccccct ctatggagta atctggggac ccaggagtgg aagagagta     420 ggggctttgt ggtgctggga gccgaggaag aatgaaatgt gcagttgagt gtgttgctcg    480
catcccaggg agcaatgcag tgctgattgt ctgttgctga gatagccttt tgttcggaac    540
ataaggttta agaaacacac acacgttttc tggggtctct tgttagatgt aaatgtgcgg    600
catccagacg cttactatgc agtgtaagct caattgggtt actaatcacc ccgcccaccc    660
gcaaacaatc aggatcattt gaatgggaac ctcattcaac ttctaggctg agagtattgc    720
cttcaaccta tttcattcta gactaagcaa ccattcaact gagataataa agcaaacaat    780
aaccnttgat catgatgtct accaaaaaat gtgccccgga aaagttcttt aggaattgta    840
atgagaaaaa naaatgaaat ggggcataaa ttctctt                             877

<210> SEQ ID NO 8
<211> LENGTH: 867
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(867)
<223> OTHER INFORMATION: n = A,T,C or G

<400> SEQUENCE: 8
gagngnnnnn cttgatctct tgnaatgaca cgccagctcg aaataaccct cactaaaggg     60
aacaaaagct ggagctccac cgcggtggcg gccgctctag aactagtgga tcccccgggc    120
tgcaggaatt cggcacgaga aaagttccag caaatataca cacactataa atatatgtga    180
atttaaaaat gtaatactca ggttaataga agaaagcaaa acatcttaag tgaacccatc    240

```
acaggatttt ccagtttgtc tctactgtag agctagatca ctgaggagat gtatgaacca      300
cactaatatc ctttgacagt acctgcattt gagtgtcatt ctgagcaaat tgagtaattt      360
tactcaatga ggtcatgatc ttcactagct tttgtggttt tttttctttc ttttttctt      420 ttttttttt tagggaaag ggtggtacat aaggacttct tagtaacttt attgaagtga      480
aaatcatgac ccttatactg caattttatg gaagcattaa aaaattatct tgtcactaat      540
ttgcattatt gtaagaacta cctcagattt ttgtgagtaa tatgaaagaa aaagtctagt      600
ttcataaaca gctactaagt tctagaatgt gttttgaaac ccaggagttt ggaagaatat      660
attattagtt taatggttta ttaaaatatt taacatttaa gttcaaaact aaaaaacaat      720
atttgaaaaa ntaaattgaa tgcgttacat tttatgaaaa actatcctga tagcccttca      780
aacttctttc ctttaaagca tttgggccta catcttcctt aactttcta ncccntgcgc      840 tacctttggc tncactggat tttttn                                           867
```

METHOD AND APPARATUS FOR FLOW-THROUGH HYBRIDIZATION

1. CROSS-REFERENCE TO RELATED APPLICATIONS

This application claims the benefit of U.S. Provisional Application No. 60/135,516, filed Nov. 25, 1998, the content of which is incorporated herein in its entirety by reference.

2. FIELD OF THE INVENTION

The present invention relates to methods and apparatuses for flow-through capture and optional recovery of nucleic acids.

3. BACKGROUND OF THE INVENTION

Nucleic acid hybridization, i.e., the ability of nucleic acid strands of complementary sequence to form duplexed hybrids, is one of the most powerful analytical techniques in the biological sciences. One of the most widely used hybridization techniques today is the "Southern blot" method discovered by Southern (Southern, 1975, J. Mol. Biol. 98:503–507). In this method, a target denatured DNA is immobilized on a filter or membrane, such as a nitrocellulose or nylon membrane. The membrane is then incubated in a buffer solution which contains a labeled oligonucleotide probe complementary to a region of the immobilized target DNA under conditions wherein the target and probe hybridize. Following wash steps, the presence or absence of hybridization is determined by detecting the label, with a positive detection indicating the presence of hybridization. The above method has also been used with immobilized RNA targets. When used with RNA the method is called "Northern blotting."

While powerful methods, Southern and Northern blotting suffer from several drawbacks. First, the methods cannot be used to study multiple sequences simultaneously within the same membrane in a single run, i.e., without the time-consuming procedures of repeat hybridization by different probes. Second, available membranes are generally unable to provide high immobilization efficiencies for target nucleic acid fragments containing fewer than 100 bp. Third, the hybridization kinetics are slow; oftentimes several hours or even several days are required for the probe and target to form a hybridized complex. Lastly, the Southern and Northern techniques suffer from the drawback that the target nucleic acid cannot be efficiently eluded from the membranes for subsequent use.

The slow hybridization kinetics observed with the Southern and Northern methods are thought to be caused by three main factors. First, since the whole membrane must be covered with hybridization solution, the concentration of probe available for hybridizing to the immobilized target DNA or RNA is extremely low. Since hybridization kinetics are governed by a bimolecular collision process, the dilute probe concentration has an enormous effect on the rate by which the probe "finds" and hybridizes to the target DNA or RNA. Second, the majority of the probe solution does not contact the membrane during the incubation process. This lowers the effective probe concentration even further, and also increases the likelihood that, if the target was initially double-stranded, the target strands will re-anneal at a faster rate than hybridization will occur. Third, a large proportion of the target nucleic acid is immobilized within the interior pores of the membrane, and is therefore inaccessible for hybridization. Thus, the hybridization kinetics are slowed even further by the probe having to diffuse into the pores of the membrane.

Recently, it has been postulated that hybridization can be used to sequence DNA or RNA. The sequencing by hybridization method ("SBH"), first described by Lysov et al. utilizes a set of short oligonucleotide probes of defined sequence to search for complementary sequences on a longer strand of target DNA or RNA. The hybridization pattern is then used to reconstruct the sequence of the target DNA or RNA (Lysov et al., 1988, Dokl. Acad. Nauk SSSR 303:1508–1511; see also, Bains & Smith, 1988, J. Theor. Biol. 135:303–307; Drmanac et al., 1989, Genomics 4:114–128; Strezoska et al., 1991, Proc. Natl. Acad. Sci. USA 88:10089–10093; Drmanac et al., 1993, Science 260:1649–1652).

Since the emergence of SBH, many new techniques for fabricating immobilized sets of probes have emerged. For example, Southern et al. constructed an array of 256 octanucleotides covalently attached to a glass plate using a solution-channeling device to direct the oligonucleotide probe synthesis (Southern et al., 1992, Genomics 13:1008–1017). Because the identity of the probe at each site is known, the entire array can be simultaneously hybridized with the target nucleic acid in a single assay; the hybridization pattern directly reveals the identities of all complementary probes.

In a similar vein, Pease et al. describe the use of photoprotected nucleoside phosphoramidites and light to direct the synthesis of a miniaturized array of 256 octanucleotides on a glass substrate in a spatially-addressable fashion (Pease et al., 1994, Proc. Natl. Acad. Sci. USA 91:5022–5026). The resulting miniaturized array measured 1.28×1.28 cm and took only 16 reaction cycles and 4 hours to synthesize. Like the array of Southern, the miniaturized array can be simultaneously hybridized with the target nucleic acid to reveal the identities of all complementary probes.

Dubiley et al. describe the use of oligonucleotide microchips that have been manufactured by immobilizing presynthesized oligonucleotides within polyacrylamide gel pads arranged on the surface of a microscope slide (Dubiley et al., 1997, Nucl. Acids Res. 25(12):2259–2265). The microchips have been applied to sequence analysis (Yershov et al., 1996, Proc. Natl. Acad. Sci. USA 93:4913–4918), mutation analysis (Drobyshev et al., 1997, Gene 188:45–52) and identification of microorganisms.

Hybridization with the above-described probe arrays provides at least two advantages over the Southern and Northern blotting techniques. First, since each probe is attached to a discrete site on the substrate, the target DNA or RNA can be assayed for its ability to form hybrids with a plurality of probes in a single experiment. Second, the hybridized complexes can be readily dissociated and the target nucleic acid recovered for subsequent use. However, since these methods also rely on immersion hybridization techniques, i.e., the entire substrate must be immersed in hybridization solution containing the target nucleic acid, the kinetics of hybridization are slow. Depending on the concentration and length of the target nucleic acid, the formation of hybridized complexes can take on the order of hours or even days. Moreover, the methods require a large volume of hybridization buffer, and hence quite a large quantity of target nucleic acid.

Due to the ability of nucleic acids to form duplexes with a high degree of specificity, hybridization has also been used to capture a target nucleic acid from a sample. Such methods can be used to determine whether the sample contains the target nucleic acid, to quantify the amount of target nucleic acid in the sample, or to isolate the target nucleic acid from a mixture of related or unrelated nucleic acids. To this end, capture polynucleotides capable of hybridizing to a target nucleic acid of interest have been immobilized on a variety of substrates and supports for use in capture assays.

For example, capture polynucleotides have been immobilized within the wells of standard 96-well microtiter plates (Rasmussen, et al., 1991, Anal. Chem. 198:138–142), activated dextran (Siddell, 1978, Eur. J. Biochem. 92:621–629), diazotized cellulose supports (Bunneman et al., 1982, Nucl. Acids Res. 10:7163–7180; Noyes and Stark, 1975, Cell 5:301–310) polystyrene matrices (Wolf et al., 1987, Nucl. Acids Res. 15:2911–2926) and glass (Maskos & Southern, 1992, Nucl. Acids Res. 20:261–266), to name a few. However, these systems suffer from very poor diffusion characteristics, leading to slow, inefficient hybridization.

In part to overcome the slow hybridization kinetics of available immobilization supports, the art has also attempted to immobilize capture polynucleotide on beads, including submicron latex particles (Wolf et al., 1987, supra), avidin-coated polystyrene beads (Urdea et al., 1987, Gene 61:253–264) and magnetic beads (Jakobson et al., 1990, Nucl. Acids Res. 18:3669). However, the beads are difficult to manipulate, particularly magnetic beads, which require elaborate isolation stations to retain the beads and precise liquid handling to avoid removal of the beads from solution.

While the art has attempted to overcome the manipulation problems of non-magnetic beads by packing the beads into columns, such columns are not easily assembled without the aid of unique frits or membranes to retain the beads. Moreover, while columns packed with such beads exhibit more favorable hybridization kinetics than the "immersion" techniques described above, the kinetics are nowhere near optimal, and the columns exhibit enormous back-pressure when hybridization solution is flowed through, which is most likely caused by close-packing of the beads.

Recently, flow-through hybridization devices designed to overcome the adverse kinetics of immersion hybridization methodologies have been designed. The devices utilize a capture polynucleotide immobilized on a membrane. The hybridization reaction takes place as fluids flow through the membrane. In one such device, the capture polynucleotide was immobilized on a nylon or nitrocellulose membrane using UV irradiation or through the use of a specific binding partner, such as biotin (EP 0 605 828 A1). In another such device, the capture polynucleotide, modified at its 5'-terminus with an amino group, was covalently attached to the carboxyl groups of a Biodyne™ C membrane (U.S. Pat. No. 5,741,647). Upon flowing a liquid sample containing a target nucleic acid through the membrane, rapid hybridization (i.e., on the order of minutes) was observed with each device.

Yet, these flow-through devices are not without drawbacks. The membranes used have extremely small pores (about 0.1–0.45 $\mu$m) such that even moderate flow-through rates cause significant back-pressure in the device. Moreover, the small pore size leads to clogging, which further increases the back-pressure of the device and may even lead to tearing of the membrane.

The clogging problem seriously limits the utility of the devices. For example, they cannot be used to capture nucleic acids from samples that contain cellular or large molecule contaminants such as, for example, proteins, carbohydrates, RNAs, DNA sequencing templates, etc., as these contaminants clog the pores of the membranes.

Lastly, while the devices can be used for nucleic acid capture, recovery efficiencies are too low to be useful for applications requiring post-capture recovery, such as recovery of PCR fragments, RNAs, restriction-digested DNA fragments, etc.

As the above discussion attests, there remains a need in the art for easy-to-use substrates which provide for rapid, efficient and highly specific capture of target nucleic acids, and which further permit recovery of the captured nucleic acid for subsequent use. Accordingly, these are objects of the present invention.

4. SUMMARY OF THE INVENTION

These and other objects are furnished by the present invention, which in one aspect provides an apparatus for rapidly, efficiently and specifically capturing, and optionally recovering, nucleic acids. In its broadest sense, the apparatus of the invention comprises a porous substrate which has a capture polynucleotide immobilized thereon, typically by way of a covalent bond between the 5'- or 3'-terminus of the capture polynucleotide and a reactive group on the porous substrate, either with or without the aid of one or more linkers. To permit high flow-through rates, the porous substrate generally has an average pore size of about 1 $\mu$m to 250 $\mu$m and a porosity of about 25% to about 80%. The density or surface concentration of immobilized capture polynucleotide is preferably in the range of about $2\times10^{-19}$ to $2\times10^{-15}$ nmole/nm$^2$ The porous substrate is optionally disposed within a housing, such as a chromatography column, spin column, syringe-barrel, pipette, pipette tip, 96 or 384-well plate, microchannels, capillaries, etc., which aids the flow of liquids through the porous substrate.

In use, a sample containing or suspected of containing a target nucleic acid capable of hybridizing to the capture polynucleotide is flowed through the porous substrate under conditions wherein the target nucleic acid and capture polynucleotide hybridize. Quite surprisingly, it has been found that the sample need only contact the porous substrate for less than a minute, typically on the order of only 3 to 15 sec., for efficient hybridization to occur, although longer contact times may be used. Following optional wash steps, the presence or absence of hybridization can then be determined.

In one embodiment of the invention, the presence of hybridization is determined by analyzing the porous substrate for the presence of a hybridization-induced detectable signal, such as, for example, fluorescence or chemiluminescence. In another embodiment of the invention, the presence of hybridization is determined by dissociating the hybridized complex, recovering the dissociated target nucleic acid and detecting the presence of the dissociated target nucleic acid.

The flow-through hybridization apparatus of the invention can be used in a wide variety of applications where knowledge about the presence or quantity of a particular target nucleic acid in a sample is desired, or where the capture of a particular target nucleic acid is desired. Thus, in another aspect, the present invention provides methods of using the flow-through hybridization apparatus to determine whether a target nucleic acid is present in a sample. Generally, the method comprises the steps of:

(a) providing a porous substrate having a capture polynucleotide capable of hybridizing to a target nucleic acid immobilized thereon;

(b) flowing a sample suspected of containing the target nucleic acid through the porous substrate under conditions wherein the target nucleic acid and capture polynucleotide hybridize; and (c) detecting the presence of hybrids, wherein a positive detection indicates the sample contains the target nucleic acid.

In another aspect, the present invention provides a method of capturing a target nucleic acid present in a sample. In general, the method comprises the steps of:

(a) providing a porous substrate having a capture polynucleotide capable of hybridizing to the target nucleic acid immobilized thereon; and (b) flowing a sample containing or suspected of containing the target nucleic acid through the porous substrate under conditions wherein the target nucleic acid and capture polynucleotide hybridize, thereby capturing the target nucleic acid. Following capture, the target nucleic acid can be optionally recovered by dissociating the hybridized complex and used in subsequent methods, such as for example, sequencing.

In a final aspect, the invention provides kits for a variety of capture applications. Generally, the kits comprise a three dimensional porous substrate of the invention having immobilized thereon a capture polynucleotide capable of hybridizing with a target nucleic acid of interest and one or more other reagents or components useful for performing a particular assay. Alternatively, the kits can comprise a three dimensional porous substrate activated with a reactive functional group and a capture polynucleotide modified with a group capable of forming a covalent linkage with the activated porous substrate, or means for synthesizing a capture polynucleotide on the activated substrate, such as nucleoside phosphoramidites and/or other DNA or RNA synthesis reactants or reagents. Optional components that can be included with the kits include housings in which the substrates can be disposed, sequencing templates and dideoxynucleotide reagents and enzymes for generating sequencing ladders from the target nucleic acid, polymerases and primers for amplifying the target nucleic acid, linkers for spacing the target nucleic acid from the porous substrate and buffers and reagents useful for sequencing, amplification and/or other nucleic acid applications.

5. BRIEF DESCRIPTION OF THE DRAWINGS

FIG. 1 illustrates the nucleotide sequences of the forward and reverse primers used in the duplex sequencing reaction according to the Example described in Section 7 (SEQ ID NOS:3, 4, 5 and 6); and FIGS. 2A1, 2A2, 2B1, 2B2 and 2B3 together provide a graph illustrating the fluorescence sequencing ladder generated by the duplex sequencing reaction of the Example described in Section 7, following capture using a flow-through hybridization apparatus according to the invention (SEQ ID NOS:7 and 8).

6. DETAILED DESCRIPTION OF THE INVENTION

The present invention provides a flow-through substrate and apparatus which permits rapid, efficient and specific capture, and optional recovery, of a target nucleic acid from a sample, and methods of using the flow-through substrate and apparatus in a variety of biological applications. As discussed in the Background section, flow-through hybridization apparatuses useful for capturing target nucleic acids have recently been developed. However, these apparatuses, which typically utilize conventional nylon and nitrocellulose hybridization membranes, suffer from several serious limitations.

For example, the membranes used in these devices typically have extremely small pore sizes (on the order of 0.1 $\mu$m or less) and are very thin (typically about 160 $\mu$m). Thus, they operate essentially as "two-dimensional" filters, and consequently have very small sample capacities. In addition, due in part to their small pore sizes, the membranes have restrictive flow rates and become readily clogged by cellular or large molecule contaminants present in the samples (e.g., proteins, carbohydrates, RNAs, large sequencing templates, etc.), severely limiting their utility in a variety of biological applications.

Moreover, once captured, the target nucleic acid cannot be efficiently recovered from the membrane for subsequent use. Thus, the devices are not useful for hybridization-based nucleic acid purification and recovery. Lastly, methods employing these flow-through devices are difficult and labor-intensive to perform, and require skilled technicians and special handling procedures and storage conditions.

Thus, while these flow-through devices can be used to rapidly capture nucleic acids, not only must they be used by skilled workers with extreme care, they cannot be used in applications which require efficient recovery of the captured target nucleic acid, such as recovery of sequences amplified by the polymerase chain reaction (PCR) or capture of hybridization sequencing ladders, or in applications in which the samples contain cellular or large molecule contaminants.

Quite surprisingly, it has now been discovered that the use of certain porous substrates in conjunction with flow-through hybridization techniques solves the above-discussed problems. Significantly, it has now been discovered that through the use of certain porous substrates, target nucleic acids can be efficiently and very rapidly captured with a very high degree of specificity. Moreover, once captured, the target nucleic acids can be efficiently and quantitatively recovered from the porous substrate for subsequent use.

6.1 The Invention

As will be discussed more thoroughly below, the porous substrate of the invention can be composed of any material or mixture of materials that will not deform, that will remain solid while in use (i.e., materials which will not dissolve in solvents used to synthesize, deprotect and/or immobilize nucleic acids, or melt under the temperatures used to hybridize and/or denature nucleic acids), and that can be derivatized or activated with a number of reactive groups sufficient for immobilization of the capture polynucleotide. Exemplary suitable materials include, for example, acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nylons (including nylon 6, nylon 6/6, nylon 6/6–6, nylon 6/9, nylon 6/10, nylon 6/12, nylon 11 and nylon 12), polycarylonitrile (PAN), polyacrylate, polycarbonate, polybutylene terephthalate (PBT), polyethylene terephthalate (PET), polyethylene (including low density, linear low density, high density, cross-linked and ultra-high molecular weight grades), polypropylene homopolymer, polypropylene copolymers, polystyrene (including general purpose and high impact grades), polytetrafluoroethylene (PTFE), fluorinated ethylene-propylene (FEP), ethylene-tetrafluoroethylene (ETFE), perfluoroalkoxyethylene (PFA), polyvinyl fluoride (PVA), polyvinylidene fluoride (PVDF), polychlorotrifluoroethylene (PCTFE), polyethylene-chlorotrifluoroethylene (ECTFE), polyvinyl alcohol (PVA), silicon styrene-acrylonitrile (SAN), styrene maleic anhydride (SMA), metal oxides and glass. A preferred material is high density or ultra-high molecular weight polyethylene.

As its name implies, the porous substrate is porous. Preferably, the average pore size and porosity will be large enough to permit rapid flow-through without causing significant back pressure under pressurized application of sample when the porous substrate is disposed within a housing. To this end, it has been discovered that porous substrates having an average pore size in the range of 1 μm to 250 μm work quite well, with those having an average pore size in the range of about 10 μm to 100 μm being preferred.

Also important in the choice of material is its porosity, as the rate of sample flow-through as well as the surface area of the substrate, and hence density of capture polynucleotide that can be immobilized on the substrate, depend in part on this factor. Generally, for porous substrates having the pore sizes described above, a porosity of between about 25% to 80% has been found to work quite well.

As will be apparent to those of skill in the art, numerous combinations of pore sizes and porosities can be used to obtain porous substrates according to the invention. Because certain densities of immobilized capture polynucleotide must be achieved to attain favorable hybridization kinetics (discussed infra), combinations of pore sizes and porosities that are capable of yielding an activated surface area of reactive groups prior to immobilization of capture polynucleotide of between about $6.7 \times 10^{-17}$ to $9.0 \times 10^{-15}$ nmol/nm$^2$ should be selected.

One of the advantages of the flow-through substrates of the invention over other flow-through membranes used in the art is their "three-dimensional" character. Quite unlike the nylon and nitrocellulose membranes used in conventional flow-through hybridization devices, which have thicknesses on the order of about 100–200 μm, the porous substrates of the invention typically have thicknesses in the range of 0.5 to 20 mm, or are even thicker. Thus, unlike the membranes of the art, which operate like two-dimensional filters, the porous substrates of the invention operate more like three-dimensional columns, and as a consequence, have significantly higher sample capacities than the membranes used in the art.

The actual thickness selected will depend, in part, on the properties of the polymeric material composing the substrate, the particular application of use and the viscosity of the sample. Preferably, a thickness is selected such that the porous substrate will not deform under pressurized application of the sample of interest. Adjusting the thickness of the porous substrate for optimal performance for a particular application is well within the capabilities of those of skill in the art.

Porous substrates having the required average pore sizes, porosities and thicknesses can be conveniently prepared from suitable materials using conventional fabrication processes such as weaving, sintering, physical binding, powder packing and gluing, as are well known in the art. For example, particles of a polymer, glass or a metal oxide having an average diameter in the range of about 0.1 μm to about 3000 μm can be sintered together to form a porous three-dimensional macroscopic network having the above-described properties.

Additionally, materials having suitable average pore sizes and porosities are available commercially, and are either available in suitable thicknesses or can be cut into slabs, strips, disks or other convenient shapes of suitable thickness. Suitable commercially available substrates include, for example, the ultra high molecular weight porous sintered polyethylene membranes available from Porex Technologies, Fairburn, Ga. (6 μm to 130 μm ave. pore size; 1/16" to 1/4" thick; 30–50% porosity); the high density polyethylene and non-cross-linked polystyrene sintered membranes available from the GenPore Division of General Polymeric Corporation, Reading, Pa. (6 μm to 130 μm ave. pore size; 1/16" to 1/4" thick; 30–50% porosity); the porous sintered plastic fiber membranes available from DeWal Industries, Saunderstown, R.I. (10 μm to 100 μm ave. pore size; 0.005" to 0.125" thick; 30–50% porosity). Preferred porous substrates are the porous sintered polyethylene membranes available from Porex Technologies, Fairburn, Ga., having an average pore size of 15 μm to 40 μm, a thickness of 1/8" and a porosity of 46% (catalogue numbers porex 4925 or porex 4901).

A capture polynucleotide is immobilized on the porous substrate. The only requirement of the capture polynucleotide is that it be capable of hybridizing to a region of the target nucleic acid under the desired hybridization assay conditions. In other words, the capture polynucleotide must be at least partially complementary to a region of the target nucleic acid, depending on the requirements of the particular application. Preferably, the capture polynucleotide is 100% complementary to a region of the target nucleic acid such that it hybridizes to the target nucleic acid with a high degree of specificity when washed under conditions of high stringency, as will be discussed more thoroughly, below.

The capture polynucleotide may be composed entirely of deoxyribonucleotides, entirely of ribonucleotides, or may be composed of mixtures of deoxy- and ribonucleotides. However, due to their stability to RNases and high temperatures, as well as their ease of synthesis, capture polynucleotides composed entirely of deoxyribonucleotides are preferred.

The capture polynucleotide may be composed of all natural or all synthetic nucleotide bases, or a combination of both. While in most instances the capture polynucleotide will be composed entirely of the natural bases (A, C, G, T or U), in certain circumstances the use of synthetic bases may be preferred. Moreover, while the backbone of the capture polynucleotide will typically be composed entirely of "native" phosphodiester linkages, it may contain one or modified linkages, such as one or more phosphorothioate, phosphoramidite or other modified linkages. As a specific example, the captive polynucleotide may be a peptide nucleic acid (PNA), which contains amide interlinkages. Additional examples of modified bases and backbones that can be used in conjunction with the invention, as well as methods for their synthesis can be found, for example, in Uhlman & Peyman, 1990, Chemical Review 90(4):544–584; Goodchild, 1990, Bioconjugate Chem. 1(3):165–186; Egholm et al., 1992, J. Am. Chem. Soc. 114:1895–1897; Gryaznov et al., J. Am. Chem. Soc. 116:3143–3144, as well as the references cited in all of the above.

While the capture polynucleotide will often be a contiguous stretch of nucleotides, it need not be. Stretches of nucleotides can be interrupted by one or more linker molecules that do not participate in sequence-specific base pairing interactions with the target nucleic acid. The linker molecules may be flexible, semi-rigid or rigid, depending on the desired application. A variety of linker molecules useful for spacing one molecule from another or from a solid surface have been described in the art (and are described more thoroughly infra); all of these linker molecules can be used to space regions of the capture polynucleotide from one another. In a preferred embodiment of this aspect of the invention, the linker moiety is from one to ten, preferably two to six, alkylene glycol moieties, preferably ethylene glycol moieties.

While the capture polynucleotide can be any number of nucleotides in length, it will typically be composed of a number of nucleotides sufficient to permit efficient, specific hybridization at moderate temperatures, while at the same time minimizing the occurrence of secondary structure. Generally, the capture polynucleotide will be composed of about 7 to 40 nucleotides, typically about 10 to about 25 nucleotides, and preferably about 15 to about 20 nucleotides.

The capture polynucleotide can be isolated from biological samples, generated by PCR reactions or other template-specific reactions, or made synthetically. Methods for isolating polynucleotides from biological samples and/or PCR reactions are well-known in the art, as are methods for synthesizing and purifying synthetic polynucleotides. Capture polynucleotides isolated from biological samples and/or PCR reactions may, depending on the desired mode of immobilization, require modification at the 3'- or 5'-terminus, or at one or more bases, as will be discussed more thoroughly below. Moreover, since the capture polynucleotide must be capable of hybridizing to the target nucleic acid, if not already single stranded, it should preferably be rendered single stranded, either before or after immobilization on the porous substrate.

The capture polynucleotide can be immobilized on the porous substrate using a wide variety of techniques. For example, the capture polynucleotide can be adsorbed or otherwise non-covalently associated with the substrate; it may be covalently attached to the substrate; or its association may be mediated by specific binding pairs, such as biotin and streptavidin. Of these methods, covalent attachment is preferred.

In order to effect covalent attachment, the substrate must first be activated, i.e., treated so as to create reactive groups on or within the substrate that can react with the capture polynucleotide to form a covalent linkage. Those of skill in the art will recognize that the desired reactive group will depend on the chemistry used to attach the capture polynucleotide to the porous substrate and the composition of the porous substrate. Typical reactive groups useful for effecting covalent attachment of the capture polynucleotide to the porous substrate include hydroxyl (—OH), sulfonyl (—SH), amino (—NH$_2$) epoxy

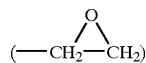

and carboxyl (—COOH) groups; however, other reactive groups as will be apparent to those having skill may also be used and are also included within the scope of the invention.

A critical feature of the porous substrate of the invention is that it be activated with a high density of reactive groups. Specifically, if the density or surface concentration of reactive groups is too low, the quantity of capture polynucleotide immobilized on the porous substrate is insufficient to hybridize a detectable quantity of target nucleic acid; if the density or surface concentration of reactive groups is too high, the reactive groups may be sterically unavailable for immobilization of capture polynucleotide and/or the immobilized capture polynucleotide may be packed too closely and may sterically prevent hybridization.

Moreover, while not intending to be bound by any particular theory of operation, it is believed that the density or surface concentration of immobilized capture polynucleotide plays an important role in the observed hybridization kinetics—high densities or surface concentrations of immobilized capture polynucleotides are believed to, in part, account for the very rapid and highly efficient hybridization capture observed with the substrates of the invention.

Since the quantity of immobilized capture polynucleotide is related to the quantity of reactive groups on the activated porous substrate, the density or surface concentration of reactive groups on the activated porous substrate plays a critical role in the ultimate hybridization kinetics achieved with the porous substrates described herein.

Generally, porous substrates activated with about $6.7 \times 10^{-17}$ nmol/nm$^2$ to about $9 \times 10^{-15}$ nmol/nm$^2$ reactive groups yield good results, i.e. quantities of capture polynucleotide which provide extremely rapid hybridization kinetics (on the order of from 5 to 15 sec.) and detectable quantities of hybridized target nucleic acid are readily immobilized thereon. Typically, the activated porous substrates will contain from about $1.34 \times 10^{-16}$ nmol/nm$^2$ to about $6.7 \times 10^{-15}$ nmol/nm$^2$ reactive groups and preferably from about $2 \times 10^{-16}$ nmol/nm$^2$ to about $3.4 \times 10^{-15}$ nmol/nm$^2$ reactive groups.

A variety of techniques for generating appropriate densities or surface concentrations of reactive groups on myriad types of substrate materials are known in the art, and include, for example chemical activation, corona discharge activation, flame treatment activation, gas plasma activation and plasma enhanced chemical vapor deposition (PECUD). Any of these techniques can be used to activate the porous substrates of the invention, provided that a sufficient density or surface concentration of reactive groups is achieved, as discussed above. Concentrations of reactive groups achieved via any mode of activation can be determined using standard methods for the particular group generated. For example, the activated porous substrates can be reacted with a reporter moiety that provides a quantifiable signal. Non-limiting examples include moieties that bear a radioactive label, moieties that bear a fluorescence label and moieties that, when cleaved from the substrate, can be conveniently quantified using conventional spectroscopic techniques, such as, for example, fluorescence and/or absorbance spectroscopy.

It has been found that due to the three-dimensional structure of the porous substrate, signals from reporter molecules bound thereto can be quenched. Thus, when quantifying reactive groups using support-bound reporter moieties, moieties producing signals that are not readily quenched should be selected, such as gamma-emitting radiolabels (e.g., $^{125}$I). More preferably, cleavable reporter moieties should be used.

One example of a cleavable reporter moiety useful for quantifying hydroxyl groups is dimethoxytrityl (DMT). A porous substrate activated with hydroxyl groups is reacted with dimethoxytrityl chloride or other DMT-containing molecule (e.g., a 5'-ODMT-3'-nucleoside phsophoramidite) using conventional methods. The DMT group is then cleaved from the substrate using conventional methods (e.g., 3% trichloroacctic acid in dichloromethane), and the cleaved DMT quantified by absorbance.

Suitable cleavable reporter moieties useful for quantifying other types of reactive groups and/or other methods for quantifying reactive groups on an activated porous substrate will be apparent to those of skill in the art.

For a review of the myriad techniques that can be used to activate the porous substrates of the invention with a sufficient density of reactive groups, see, the Wiley Encyclopedia of Packaging Technology, 2d Ed., Brody & Marsh, Ed., "Surface Treatment," pp. 867–874, John Wiley & Sons (1997), and the references cited therein (hereinafter "Surface Treatment"). Chemical methods suitable for generating amino groups on silicon oxide substrates are described in Atkinson & Smith, "Solid Phase Synthesis of Oligodeoxyribonucleotides by the Phosphite Triester Method," In: Oligonucleotide Synthesis: A Practical Approach, M J Gait, Ed., 1984, IRL Press, Oxford, particularly at pp. 45–49 (and the references cited therein); chemical methods suitable for generating hydroxyl groups on silicon oxide substrates are described in Pease et al., 1994, Proc. Natl. Acad. Sci. USA 91:5022–5026 (and the references cited therein); chemical methods for generating functional groups on polymers such as polystyrene, polyamides and grafted polystyrenes are described in Lloyd-Williams et al., 1997, Chemical Approaches to the Synthesis of Peptides and Proteins, Chapter 2, CRC Press, Boca Raton, Fla. (and the references cited therein).

Due to its ability to reproducibly generate the densities or surface concentrations of reactive groups discussed above on a variety of substrate materials, a particularly preferred method for activating the porous substrates of the invention is plasma activation. Plasmas are partially ionized gases containing free radicals, electrons and neutral species that, in use, can be extremely well-controlled and characterized, and are highly reproducible. An advantage of plasma activation is that since only a few angstroms of the surface layer of the plastic are modified, the bulk mechanical and physical properties of the plastic remain unchanged. Moreover, plasma activation is extremely versatile, permitting a wide variety of surface functional groups, concentrations and architectures to be explored using the same substrate.

Generally, plasma activation involves placing the plastic to be activated in an evacuated chamber. A process gas is fed into the chamber at a desired pressure and plasma is created by applying radio-frequency (RF) energy across the chamber. The plasma contains excited gas species (including electrons, atoms, molecules, ions and free radicals) which can break covalent bonds and react with the polymer molecules on the surface of the plastic structure.

The composition of the gas and process variables such as gas pressure, level of RF energy applied and time have a strong influence on the composition of the resulting surface. The surface reactivity of the plastic substrate can be sufficiently long-lived that, even after removal from the plasma chamber, the activated surfaces can also be functionalized by exposure to additional reagents that are capable of reacting with the activated surface.

A wide variety of techniques exist for using plasmas to activate myriad types of substrate materials with reactive groups suitable for immobilization of capture polynucleotides, including hydroxyl, amino and carboxyl reactive groups. The methods include among others, cross-linking and activation (see, e.g., Surface Treatment, supra, at pages 870–872, and the references cited therein). Any of the available art-known plasma activation methods, or later discovered plasma activation methods, can be used to activate the porous substrates of the invention.

Methods suitable for activating a variety of porous substrates with hydroxyl groups are described in U.S. Pat. No. 5,700,559 and are also available from Metroline Industries, Inc. (Corona, Calif.). Methods suitable for activating a polyethylene porous substrate with carboxyl groups or amine groups are provided in the Examples section.

Once activated, the capture polynucleotide can be immobilized on the porous substrate. In one embodiment of the invention, the capture polynucleotide is chemically synthesized in situ directly onto the activated porous substrate. Those of skill in the art will recognize that when using direct chemical synthesis, the covalent bond formed between the capture polynucleotide and the porous substrate must be substantially stable to the synthesis and deprotection conditions so as to avoid loss of the capture polynucleotides during synthesis and/or deprotection. One such stable bond is the phosphodiester bond, which connects the various nucleotides in a polynucleotide, and which can be conveniently formed using well-known chemistries (see, e.g., Gait, Oligonucleotide Synthesis: A Practical Approach, 1984, IRL Press, Oxford, England). Other stable bonds suitable for use with hydroxyl-activated porous substrates include phosphorothiate, phosphoramidite, or other modified nucleic acid interlinkages. For porous substrates modified with amino groups, the bond could be a phosphoramidate, amide or peptide bond. When porous substrates are activated with epoxy functional groups, a stable C—N bond could be formed. Suitable reagents and conditions for forming such stable bonds are well known in the art.

In one particularly convenient embodiment, the capture polynucleotide is synthesized directly on a hydroxyl-activated porous substrate using commercially available phosphoramidite synthesis reagents and standard oligonucleotide synthesis chemistries. In this mode, the capture polynucleotide is covalently attached to the porous substrate via its 3'-terminus by way of a phosphodiester linkage. When the size of the porous substrate permits, commercially available automated synthesizers may be employed to synthesize the capture polynucleotide directly on the activated porous substrate.

The density of capture polynucleotide covalently attached to the porous substrate can be conveniently controlled by adding an amount of the first synthon (e.g., N-protected 5'-O-dimethoxytrityl-2'-deoxyribonucleotide-3'-O-phosphoramidite) sufficient to provide the desired number of synthesis groups on the substrate, and capping any unreacted hydroxyl groups on the substrate with a capping reagent (e.g., 1,4-diaminopyridine; DMAP). After the excess hydroxyls have been capped, the trityl group protecting the 5'-hydroxyl can be removed and synthesis of the capture polynucleotide carried out as usual. Thus, due to its high extinction coefficient, the removed trityl group can be conveniently used to quantitate the number of polynucleotides on the activated substrate by uv/vis spectrometry. Following synthesis, the capture polynucleotide is deprotected using conventional methods.

In an alternative embodiment, the capture polynucleotide is covalently attached to the activated porous substrate through a post-synthesis or post-isolation conjugation reaction. In this embodiment, a pre-synthesized or isolated capture polynucleotide which is modified at its 3'-terminus, 5-terminus and/or at one of its bases with a reactive functional group (e.g. epoxy, sulfonyl, amino or carboxyl) is conjugated to an activated porous substrate via a condensation reaction, thereby forming a covalent linkage. Again, substantially stabile (i.e., non-labile) covalent linkages such as amide, phosphodiester and phosphoramidate linkages are preferred. Synthesis supports and synthesis reagents useful for modifying the 3'- and/or 5'-terminus of synthetic polynucleotides, or for incorporating a base modified with a reactive group into a synthetic polynucleotide, are well-known in the art and are even commercially available.

For example, methods for synthesizing 5'-modified oligonucleotides are described in Agarwal et al., 1986, Nucl. Acids Res. 14:6227–6245 and Connelly, 1987, Nucl. Acids Res. 15:3131–3139. Commercially available products for synthesizing 5'-amino modified oligonucleotides include the N-TFA-C6-AminoModifer™, N-MMT-C6-

AminoModifer™ and N-MMT-C12-AminoModifier™ reagents available from Clontech Laboratories, Inc., Palo Alto, Calif.

Methods for synthesizing 3'-modified oligonucleotides are described in Nelson et al., 1989, Nucl. Acids Res. 17:7179–7186 and Nelson et al., 1989, Nucl. Acids Res. 17:7187–7194.

Commercial products for synthesizing 3'-modified oligonucleotides include the 3'-Amino-ON™ controlled pore glass and Amino Modifier II™ reagents available from Clontech Laboratories, Inc., Palo Alto, Calif.

Other methods for modifying the 3' and/or 5' termini of oligonucleotides, as well as for synthesizing oligonucleotides containing appropriately modified bases are provided in Goodchild, 1990, Bioconjugate Chem. 1:165–186, and the references cited therein. Chemistries for attaching such modified oligonucleotides to substrates activated with appropriate reactive groups are well-known in the art (see, e.g., Ghosh & Musso, 1987, Nucl. Acids Res. 15:5353–5372; Lund et al., 1988, Nucl. Acids Res. 16:10861–10880; Rasmussen et al., 1991, Anal. Chem. 198:138–142; Kato & Ikada, 1996, Biotechnology and Bioengineering 51:581–590; Timofeev et al., 1996, Nucl. Acids Res. 24:3142–3148; O'Donnell et al., 1997, Anal. Chem. 69:2438–2443).

Methods and reagents for modifying the ends of polynucleotides isolated from biological samples and/or for incorporating bases modified with reactive groups into nascent polynucleotides are also well-known and commercially available. For example, an isolated oligonucleotide can be phosphorylated at the 5'-terminus with phosphorokinase and this phosphorylated oligo covalently attached onto an amino-activated porous substrate through a phosphoramidate or phosphodiester linkage. Other methods will be apparent to those of skill in the art.

In one convenient embodiment of the invention, a capture polynucleotide modified at the 3'- or 5'-terminus with a primary amino group is conjugated to a carboxy-activated porous substrate. Chemistries suitable for forming carboxamide linkages between carboxyl and amino functional groups are well-known in the art of peptide chemistry (see, e.g., Atherton & Sheppard, Solid Phase Peptide Synthesis, 1989, IRL Press, Oxford, England and Lloyd-Williams et al., Chemical Approaches to the Synthesis of Peptides and Proteins, 1997, CRC Press, Boca Raton, Fla. and the references cited therein). Any of these methods can be used to conjugate the amino-modified capture polynucleotide to the carboxy-activated porous substrate.

In a preferred embodiment, the carboxamide linkage is generated using N,N,N',N'-tetramethyl (succinimido) uronium tetrafluoroborate ("TSTU") as a coupling reagent. Reaction conditions for the formation of carboxyamides with TSTU that can be used in conjunction with nucleic acids are described in Knorr et al., 1989, Tet. Lett. 30(15):1927–1930; Bannworth & Knorr, 1991, Tet. Lett. 32(9):1157–1160; and Wilchek et al., 1994, Bioconjugate Chem. 5(5):491–492. Preferred reaction conditions are provided in the examples.

The choice of immobilizing the capture polynucleotide on the porous substrate via its 3'- or 5'-end will depend upon the particular application. For capture and subsequent release for further processing such as sequencing or amplification (e.g., PCR), 3'-immobilization is preferred. For capture and direct amplification on the substrate, 5'-immobilization is preferred. For diagnostic applications, the terminus of immobilization will depend upon the target selection.

Whether synthesized directly on the activated substrate or immobilized on the activated substrate post-synthesis or post-isolation, the capture polynucleotide can optionally be spaced away from the porous substrate by way of one or more linkers. As will be appreciated by those having skill in the art, such linkers will be at least bifunctional, i.e., they will have one functional group or moiety capable of forming a linkage with the activated substrate and another functional group or moiety capable of forming a linkage with another linker molecule or the capture polynucleotide. The linkers may be long or short, flexible or rigid, charged or uncharged, hydrophobic or hydrophilic, depending on the particular application.

In certain circumstances, such linkers can be used to "convert" one functional group into another. For example, an amino-activated porous substrate can be converted into a hydroxyl-activated porous substrate by reaction with, for example, 3-hydroxy-propionic acid. In this way, substrate materials which cannot be readily activated with a specified reactive functional group can be conveniently converted into a an appropriately activated porous substrate. Chemistries and reagents suitable for "converting" such reactive groups are well-known, and will be apparent to those having skill in the art of organic chemistry.

Linkers can also be used, where necessary, to increase or "amplify" the number of reactive groups on the activated porous substrate. For this embodiment, the linker will have three or more functional groups. Following attachment to the activated substrate by way of one of the functional groups, the remaining two or more groups are available for attachment of capture polynucleotide. Amplifying the number of functional groups on the activated porous substrate in this manner is particularly convenient when the substrate has been chemically activated. Amplification is generally not necessary when the substrate has been plasma activated.

Reagents for amplifying the number of reactive groups are well-known and will be apparent to those of skill in the art. A particularly convenient class of amplifying reagents are the multifunctional epoxides sold under the trade name DENACOL™ (Nagassi Kasei Kogyo K.K.). These epoxides contain as many as four, five, or even more epoxy groups, and can be used to amplify porous substrate activated with reactive groups that react with epoxides, including, for example, hydroxyl, amino and sulfonyl activated porous substrates. The resulting epoxy-activated substrate can be conveniently converted to a hydroxyl-activated substrate, a carboxy-activated substrate, or other activated substrate by well-known methods.

Linkers suitable for spacing biological molecules such as polynucleotides from solid surfaces are well-known in the art, and include, by way of example and not limitation, polypeptides such as polyproline or polyalanine, saturated or unsaturated bifunctional hydrocarbons such as 1-amino-hexanoic acid, polymers such as polyethylene glycol, etc. A particularly preferred linker is polyethylene glycol (MW 100 to 1000). 1,4-Dimethoxytrityl-polyethylene glycol phosphoramidites useful for forming phosphodiester linkages with hydroxyl groups, as well as methods for their use in nucleic acid synthesis on solid substrates, are described, for example in Zhang et al., 1991, Nucl. Acids Res. 19:3929–3933 and Durand et al., 1990, Nucl. Acids Res. 18:6353–6359. Other methods of attaching polyethylene glycol linkers will be apparent to those of skill in the art.

The amount of capture polynucleotide immobilized on the activated porous substrate will depend in part upon the surface density of available functional groups and efficiency of the immobilized capture polynucleotide. As the amount of immobilized capture polynucleotide can affect the hybridization kinetics, immobilization methods that yield a surface density of immobilized capture polynucleotide in the range of $2\times10^{-19}$ to $2\times10^{-15}$ nmol/nm$^2$ should be employed. Preferably, the surface density of immobilized capture polynucleotide should be about $6\times10^{-17}$ to $6\times10^{-16}$ nmol/nm$^2$. The density can be measured by well-known methods, including radioactivity measurements, fluorescence measurements, UV absorption, or chemical means.

It has been discovered that in some circumstances, signals such as radioactivity and fluorescence are partially quenched by the substrate. While not intending to be bound by any particular theory, it is believed that the three-dimensional nature of the substrate quenches the signal. Radioactivity or fluorescence from capture polynucleotides immobilized within the pores of the porous substrate most likely cannot travel through the substrate to produce a detectable signal.

Thus, in a preferred embodiment, the quantity of capture polynucleotide immobilized on the porous substrate is determined by quantifying the amount of a labeled complementary polynucleotide that hybridizes to the porous substrate. In such an assay, a porous substrate of known area is immersed in a solution containing a saturating or excess quantity of a labeled complementary polynucleotide under conditions which favor sequence specific hybridization and which disfavor non-specific binding for a time period sufficient for hybridization to occur. The complementary polynucleotide can be labeled with any type of label that can be conveniently quantified, e.g., a radioactive label of known specific activity, a fluorophone, etc. Following optional wash steps to further decrease non-specific binding, the hybridization complex is disrupted, for example by application of heat above melting temperature ($T_m$) of the duplex under conditions of low salt, the labeled polynucleotide is recovered, and quantified. From this, the density of capture polynucleotide immobilized on the porous substrate can be determined.

To insure that a saturating level of labeled complementary polynucleotide has been used, multiple assays can be carried out using different concentrations of labeled polynucleotide, and the quantity of immobilized capture polynucleotide obtained for each sample. The plateau value reached for the quantity of labeled complementary polynucleotide released as a function of its concentration is the quantity of capture polynucleotide immobilized on the substrate.

Those of skill in the art will recognize that quantifying the amount of immobilized capture polynucleotide using a hybridization assay only "counts" those polynucleotide molecules that hybridize with the labeled complementary polynucleotide. Thus, the value observed may not be quantitative in a strict sense. However, quantifying the amount of capture polynucleotide immobilized using this hybridization assay has significant advantages. Most importantly, it provides insights into the quantity of capture polynucleotide that is available to participate in hybridization reactions under "real world" conditions. Thus, while the value obtained may not be strictly quantitative, all references herein to quantities of immobilized capture polynucleotide include quantities that are determined by the hybridization assay described above.

Preferred methods for immobilizing sufficient quantities of capture polynucleotides are provided in the examples.

Once the capture polynucleotide has been immobilized on the porous substrate (and deprotected as necessary), the porous substrate can be used for the capture, and optional release, of a target nucleic acid capable of hybridizing to the capture polynucleotide. The target nucleic acid is the nucleic acid to be captured and/or detected. Like the capture polynucleotide, it may be composed of ribo- or deoxyribonucleotides or mixtures thereof; natural or synthetic bases or mixtures thereof; and may contain one or more modified interlinkages. It may be double-stranded or single-stranded; if double stranded the target nucleic acid should preferably be denatured prior to application to the porous substrate.

Examples of target nucleic acids include plasmids or portions thereof, genomic DNA or portions thereof, DNA derived from subcellular organelles, cDNA, messenger and ribosomal RNAs, all of which may be isolated and prepared for use with the present invention using methods known in the art.

The target nucleic acid may be modified to contain a reporter group which can be used, for example, to detect hybridization on the porous substrate, for further purification post-capture or for other purposes as will be apparent to those having skill in the art. Useful reporter groups include radioisotopes, fluorophores, moieties that chemiluminesce, ligands capable of binding to a secondary reporter group (e.g., biotin), enzymes capable of producing a calorimetric reaction (e.g. peroxides, digoxygenine), and the like. Methods and reagents for incorporating such reporter groups into nucleic acids are well-known in the art, as are methods for detecting such reporter groups. The actual reporter group used will depend, of course, on the desired application, quantity of target nucleic acid and other factors that will be apparent to those having skill in the art.

While the substrate can be used alone, it will typically be disposed within a housing which aids the flow of hybridization solution containing the target nucleic acid through the porous substrate. When disposed within a housing, the porous substrate is configured to sealingly engage the interior surface of the housing along the entire perimeter of the substrate so that sample applied to the housing will flow through the porous substrate. Convenient housings include, for example, syringe barrels, chromatography columns, spin columns, pipettes, pipette tips, microchannels, capillaries, etc. The porous substrates can also be disposed within, or replace the bottoms of, a 96 or 384-well or other standardized multi-well plate. Moreover, the porous substrates of the invention can be used in conjunction with known immunological or other known flow-through devices with little modification in operation. Exemplary flow-through devices suitable for adaptation for use with the substrates of the invention are described, for example, in U.S. Pat. No. 4,366,241, U.S. Pat. No. 4,632,901, U.S. Pat. No. 4,818,677, U.S. Pat. No. 4,920,046, U.S. Pat. No. 5,741,647 and EP 0 605 828 A1.

In use, a sample containing or suspected of containing the target nucleic acid is applied to, and flowed through, the porous substrate. Prior to application of the sample, the porous substrate may be washed with buffer to equilibrate the porous substrate to the conditions that will be used for hybridization or capture. The porous substrate may also be treated to disrupt any secondary structure in the capture polynucleotide, either by washing with denaturing buffers or by application of heat.

While the volume of the applied sample is not critical, a sample volume equal to or less than the void volume of the porous substrate is particularly effective. Typically, a sample volume of about 1–100 $\mu$l, preferably about 20–60 $\mu$l, applied to a 7 mm diameter×3.2 mm thick disk of porous substrate provides good results.

Moreover, while the concentration of target nucleic acid in the sample can be varied over quite a wide range, preferably the number of capture sites on the porous substrate exceeds the number of target nucleic acids in the sample to be captured. Molar ratios of capture polynucleotide to target nucleic acid in the range of about 1:1 to $10^6$:1 provide good results; however, a molar ratio of about $10^3$:1 is preferred.

As the sample flows through and contacts the porous substrate, hybridization takes place. Thus, the sample should contact the porous substrate for a period of time that is long enough for hybridization to occur. The kinetics of hybridization will depend on many factors, including the GC content of the capture polynucleotide, the lengths of the capture polynucleotide and target nucleic acid, the amount of capture polynucleotide immobilized on the porous substrate, the concentration of target nucleic acid in the sample, the salt and/or buffer conditions of the sample, the temperature of hybridization, etc. As it has been discovered that hybridization occurs almost instantaneously (i.e., in a matter of seconds) under most hybridization conditions, samples incubated with the porous substrate for less than a minute, and even on the order of about 5 to 15 sec. generally gave good results.

The sample can be flowed onto the porous substrate for a period of contact and then flowed through, or it can be continuously flowed through the substrate at a flow rate sufficient to achieve the desired duration of contact. The sample can be flowed through the porous substrate under gravity, electrophoretically, electrosmotically, or with the aid of pumps, vacuum pressure or centrifugal force.

As will be recognized by those having skill in the art, the degree of specificity of hybridization achieved will vary, and will depend on, among other factors, the salt concentration of the sample, the hybridization temperature, the GC content of the capture polynucleotide, the lengths of the capture polynucleotide and target nucleic acid, the types of nucleic acids (e.g. RNA or DNA) and whether one of the nucleic acids, e.g., capture polynucleotide, is immobilized. Manipulation of variables such as buffer salt concentrations, hybridization temperature, etc. to achieve the desired degree of specificity is well within the capabilities of those having skill in the art. Guidance for selecting hybridization conditions suitable for a particular application can be found, for example, in Nucleic Acid Hybridization: A Practical Approach, Hames & Higgins, Ed., IRL Press 1985.

The target nucleic acid can be applied to the porous substrate under conditions of high stringency, i.e., under hybridization buffer and temperature conditions which discriminate between wholly and partially complementary hybrids. Temperature control can be maintained with the aid of, for example, a water bath, an incubator or a heat block. By manipulation of the hybridization buffer conditions, temperature and hybridization time (i.e., time of contact with the porous substrate), only target nucleic acids sharing a desired degree of homology with the capture polynucleotide can be captured on the porous substrate.

Alternatively, the target nucleic acid can be applied to the porous substrate under conditions of moderate or low stringency, and the desired degree of stringency achieved via washing under, for example, conditions of high stringency. It has been discovered that hybridizing the target nucleic acid and capture polynucleotide under conditions of low stringency followed by washing with buffer under conditions of moderate to high stringency generally provides good results. Hybridizing the target nucleic acid under conditions of high stringency tends to decrease non-specific binding to the substrate. Moreover, it has been discovered that applying the target nucleic acid to the porous substrate under the above-described stringency conditions yields extremely rapid hybridization kinetics—i.e., hybridization between the target nucleic acid and capture polynucleotide occurs in less than a minute, typically on the order of about 5 to 15 sec.

As further described below (see Section 7), an example of hybridization conditions that can be used in the methods of the invention involves pre-rinsing the substrate with 1× TET buffer (100 mM Tris-HCl, pH 8.0, 3 mM EDTA, 0.1% Tween™-20) and hybridization at 37° C. under conditions of moderate stringency (562.5 mM tetramethylammonium chloride, 75 mM Tris-HCl, pH 8.0, 2.25 mM EDTA, 0.075% Tween™-20) for a period of between 15 sec. to 5 min., followed by washing with 1× TET buffer and then optionally with 70% aqueous isopropanol.

Another example of standard hybridization conditions that can be used is 600 mM tetraethylammonium chloride (TMA), 3 mM EDTA, 0.03% Tween T-20 and 100 mM Tris-HCl, pH 8.0. An example of high salt lower stringency hybridization conditions is 800 mM TMA, 3 mM EDTA, 0.03% Tween™-20 and 100 mM Tris-HCl, pH 8.0. An example of reduced-salt high stringency hybridization conditions is 200 mM TMA, 3 mM EDTA, 0.03% Tween™-20 and 100 mM Tris-HCl, pH 8.0.

Additional examples of progressively higher stringency conditions are as follows: 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 15 sec. to 5 min. or longer each, preferably in the order listed above, repeating any or all of the steps listed. However, as mentioned above, optimal conditions will vary, depending on the particular hybridization reaction involved, and can be determined empirically.

Following capture and optional washing, the presence or absence of hybridization on the porous substrate can be determined. The mode of detection will depend on whether the target nucleic acid bears a reporter molecule, and on the type of reporter molecule. For example, if the target nucleic acid bears a radioisotope label, the target substrate can be detected for retained radioactivity; if the target nucleic acid bears a fluorophore label, the porous substrate can be analyzed for fluorescence; if the target nucleic acid bears a biotin label, the target substrate can be assayed for the ability to bind labeled (e.g., fluorescently labeled) avidin or streptavidin. Those of skill in the art will recognize that virtually any reporter group and detection scheme can be easily adapted for use with the present invention. In many instances, the quantity of reporter group can be determined, thereby determining the quantity of target nucleic acid present in the sample.

In circumstances where the target nucleic acid does not bear a reporter group, the presence of hybridization can be determined by contacting the porous substrate with reagents that preferentially bind to double-stranded nucleic acids. Particularly useful reagents include intercalators such as ethidium bromide; especially those intercalators which exhibit induced or shifted fluorescence upon intercalation, such as, for example, ethidium homodimers. Other useful reagents can be found, e.g., in Haugland, Handbook of Fluorescent Probes and Research Chemicals, latest edition, Molecular Probes, Inc., P.O. Box 22010, Eugene, Oreg. 97402-0469. Contacting a porous substrate that has not been subjected to hybridization with the same detection reagent provides a convenient control. The quantity of hybrid can be determined by comparing the fluorescence intensity of the substrate with that produced by known quantities of duplex DNA, preferably duplex DNA of the same length as the hybrids.

Alternatively, the presence of hybridization can be determined by dissociating the hybrids and recovering the hybridized target nucleic acid. Quite unlike other filter and flow-through hybridization methods, a significant advantage of the present invention is that the hybridized complex can be dissociated and the target nucleic acid efficiently recovered.

The hybrids can be conveniently dissociated with heat, or with chemical denaturants such as 7–8M urea, 70% $NH_4OH$ (aq.), formamide, NaOH and deionized water or by electro-elution. The recovered target nucleic acid can be detected by conventional means, such as ethidium bromide or other staining, UV absorbance, etc. Of course, if the target nucleic acid bears a reporter group, the reporter group can be used for detection after recovery.

6.2 Uses

The porous substrates of the invention can be used in virtually any application where the capture and/or recovery of a target nucleic acid is desirable. Due to their ability to provide easy and efficient recovery, the porous substrates described herein can be advantageously used to purify target nucleic acids such as PCR amplification products from a pool of related or unrelated sequences in high yield for subsequent use. Moreover, pluralities of porous substrates, each having a unique capture polynucleotide immobilized thereon, can be disposed within a single housing for simultaneous capture of a plurality of different target nucleic acids, or for SBH applications. Alternatively, a plurality of capture polynucleotides can be immobilized on a single porous substrate.

Additional uses include capture and recovery of sequencing ladders for subsequent sequencing application. In fact, because the porous substrates of the invention have fairly large pores, large sequencing templates such as BAC, YAC and gnomic sequencing templates can be recovered and sequenced without the clogging problems observed with conventional membrane-based flow-through devices. Thus, the porous substrates of the invention permit capture and subsequent sequencing of templates without regard to their sizes, thereby allowing longer templates to be sequenced than can be sequenced using conventional methods.

The porous substrates also permit capture and/or recovery of nucleic acids from biological samples or other samples containing large molecule contaminants without substantial clogging of the device. Once captured, these target nucleic acids can be directly used for PCR, sequencing, or other applications.

Moreover, the porous substrates of the invention permit washing of the captured polynucleotide. Washing removes to low levels all other reaction or sample components, such as templates, proteins, dNTPs, dye terminators, non-captured primers, salts, etc.

Thus, as will be appreciated by those of skill in the art, the porous substrates and apparatuses comprising the porous substrates can be advantageously used in any application that involves hybridization-based capture, and optimal recovery, of nucleic acids.

The invention having been described, the following examples are intended to illustrate, not limit, the invention.

7. EXAMPLE: CAPTURE AND SEQUENCING OF A DUPLEX SEQUENCING LADDER

The following example demonstrates the use of porous substrates according to the invention to selectively capture sequencing ladders generated from a region of plasmid DNA during a duplex sequencing reaction. The sequencing chemistry is very similar to that used in the standard Big Dye™ Terminator (P.E. Applied Biosystems, Foster City, Calif.) sequencing reaction, except that both forward and reverse primers are extended simultaneously. The sequencing ladders generated are then selectively separated via flow-through capture prior to sequence analysis.

The control template used was a Bluescript™ II±vector (Stratagene, La Jolla, Calif.) with a 3667 base insert. The sequences of the forward and reverse primers are provided in FIG. 1. Duplex sequencing of forward and reverse directions of a template require that the primers be approx. 1500 bases or greater apart. The extension products of short inserts are partially complementary to one another and are therefore susceptible to cross-hybridization. Partial annealing of the longer fragments of one primer to the other may occur such that both strands are captured during the hybridization.

In the protocol described below, the ready-reaction premix concentrations used were the same as those used in the standard Big Dye™ Terminator single reaction. The primers were supplied as a premix ready to be added to the reaction.

7.1 Experimental Protocol

7.1.1 Preparation of Primers

Forward and reverse sequencing primers according to FIG. 1 were prepared using standard solid-phase phosphoramidite DNA chemistry on an ABI Model 394 DNA Synthesizer (P.E. Applied Biosystems, Foster City, Calif.) according to the manufacturers protocols. For the linker sections of the molecules, DMTr—O—$(CH_2CH_2—O)_4$—$CH_2CH_2$—O-phosphoramidite (PEG phosphoramidite) was prepared as previously described (Zhang et al., 1991, supra; Durand et al., 1990, supra) and used as a standard phosphoramidite reagent at the appropriate point in the synthesis. Each linker consisted of two PEG phosphoramidite units.

7.1.2 Duplex Sequencing Reaction

A duplex sequencing reaction was carried out using standard Big Dye™ Terminator (P.E. Applied Biosystems, Foster City, Calif.) reagents and methods, except that both forward and reverse primers (FIG. 1) were used. The duplex sequencing reaction contained the following reagents:

| | |
|---|---|
| Template (400 ng/µl) | 3 µl |
| Big Dye ™ Terminator Premix | 8 µl |
| Primer Mix (2 pmol/µg each primer) | 2 µl |
| Distilled Water | 7 µl |
| Final Volume | 20 µl |

Sequencing ladders were generating using the following thermal cycling:

| | | |
|---|---|---|
| 1 cycle | preheat step | |
| | 97° C., 60 sec. | |
| 40 cycles | steps | |
| | 96° C., 10 sec. | |
| | 45° C., 15 sec. | use higher annealing temp., such as 51° C., for GC-rich templates |
| | 60° C., 4 min. | |
| 1 cycle | heat-denaturation step | this step inactivates the Taq polymerase |
| | 99.9° C., 10 min. | |
| hold cycle | 4° C. | |

7.1.3 Synthesis of 3'-Aminated Capture Polynucleotides

Forward [5'-CCGTTTGCGTGAGTG-(pentaethyleneglycol)$_2$-$(CH_2)_6$—$NH_2$—3'; SEQ ID NO:1] and reverse [5'-GTGCTCTTGGGAGAGTT-(pentaethyleneglycol)$_2$-$(CH_2)_6$—$NH_2$; SEQ ID NO:2] capture polynucleotides modified at their 3'-termini with a primary amino group were synthesized on an ABI Model 394 DNA synthesizer (P.E. Applied Biosystems, Foster City, Calif.) using 3'-amino linker controlled pore glass and standard phosphoramidite reagents according to the manufacturers' protocols. The capture polynucleotides were cleaved and deprotected with aqueous ammonium hydroxide and purified by reverse-phase HPLC.

7.1.4 Carboxy-Activation of Porous Substances

Polyethylene sheets having a porosity of 40–50% and an average pore size of 25–40 $\mu$m (Porex catalog no. 4901 or 4925) were cut with a cork borer into 7 mm diameter by 3.2 mm thick discs and plasma-activated with carboxyl groups. To activate, discs were placed into a vacuum chamber containing radio-frequency (RF) electrodes and pumped down to 50 mtorr. Argon and acrylic acid were then simultaneously introduced into the chamber at a rate of 50 sccm until the pressure in the chamber stabilized between 160–180 mtorr, corresponding to an approximately 50:50 ratio of argon:acrylic acid.

After the pressure stabilized, a plasma was generated by applying a 13.56 MHZ RF for 3 min. The RF and gases were then turned off and the chamber pumped back down to 50 mtorr. Following evacuation, the chamber was flushed with 4% $H_2$/96% He for 3 min. to quench any remaining ions and free radicals. Following quenching, the chamber was vented to atmosphere and the carboxy-activated porous substrates removed.

The carboxy-activated substrates contained 0.17 $\mu$mol carboxyl groups per gram, as determined by derivatizing with ethylene diamine followed by the ninhydrin test.

The porous substrate can also be carboxy-activated by an alternative method using an oxygen plasma treatment followed by an acrylic acid plasma-enhanced chemical vapor deposition method developed by $4^{th}$ State, Inc. (Belmont, Calif.). In this alternative method, polyethelene porous substrates (e.g., discs) are placed into a vacuum chamber and pumped down to 60 mtorr. Oxygen is then added at a rate of 250 sccm (nominal pressure of 325 mtorr) for 3 min. at 435 watts. The oxygen plasma is followed by 75 sccm argon (nominal pressure of 100 mtorr) with injection of acrylic acid to a nominal pressure of 180–200 mtorr for 3 min. at 500 watts. Lastly, the substrates are quenched in argon for 3 min. at 0 watts and then vented to atmosphere.

7.1.5 Amino-Activation of Porous Substances

The above-described polyethylene substrates (e.g., discs) can be activated with amino groups using a combination of oxygen and ammonia plasma treatment, also develped by $4^{th}$ state, Inc. (Belmont, Calif.). After pumping down to a base pressure of 60 mtorr, the polyethylene substrates are first exposed to 250 sccm oxygen (nominal pressure of 325 mtorr) for 3 min. at 435 watts. Next, the substrates are exposed to 250 sccm ammonia (nominal pressure of 325 mtorr) for 6 min. at 300 watts. Lastly, the substrates are quenched in ammonia for 1 min. (200 mtorr nominal pressure) and then vented to the atmoshpere.

7.1.6 Immobilization of Capture Polynucleotides

To convert the carboxy-activated substrates to their NHS esters, carboxy-activated substrates (0.3 g; 0.17 $\mu$mol carboxyl group per gram) were suspended in 1 ml of DMF containing TSTU and DMAP (0.25 $\mu$mole each) in a glass vial. The reaction mixture was agitated for 5 h at room temp. in the dark.

The reaction mixture was removed, the NHS-ester-activated substrates were placed in a funnel attached to a house vacuum and washed in seriatim with 10–15 ml DMF, 10–15 ml ethanol and 5–10 ml dichloromethane. Following washing, the substrates were air-dried.

The dried NHS-ester-activated substrates were suspended in a solution of sodium phosphate (0.1 M, pH 8.0) containing 3'-aminated capture polynucleotide (0.6 nmol/$\mu$l). The reaction was shaken overnight at room temp. in the dark.

The conjugation solution was removed and saved. The substrates were then washed in a funnel as previously described with 10–15 ml deionized water and 5 ml 0.4 N $NH_4OH$(aq.). The substrates were then incubated in 5–10 ml $NH_4OH$(aq.) at room temp. for 5 min., and washed with 10–15 ml 1× TET buffer (100 mM Tris-HCl, pH 8.0; 3 mM EDTA; 0.1% Tween-20™). The substrates were suspended in 1× TET buffer and stored at 4° C.

7.1.7 Hybridization Capture and Sequencing

Substrates (25) having forward capture polynucleotide (SEQ ID NO:1) immobilized thereon were disposed within white-colored spin columns; substrates (25) having reverse capture polynucleotide (SEQ ID NO:2) immobilized thereon were disposed within purple-colored spin columns. The resultant capture columns were rinsed and hybridized as follows:

1. All capture columns were fitted in 2 ml wash tubes, placed in a table-top centrifuge and spun at approx. 7000 RCF for 60 sec. The columns were pre-rinsed with 300 $\mu$l 1× TET buffer (100 mM Tris-HCl, pH 8.0, 3 mM EDTA, 0.1% Tween™-20) and spun at approx. 7000 RCF for 1 min.

2. One set of rinsed capture columns was fitted in 1.5 ml conical collection tubes. For hybridization, 10 $\mu$l of sequencing reaction (equilibrated to room temp.) was mixed with 30 $\mu$l hybridization buffer (750 mM tetramethylammonium chloride, 100 mM Tris-HCl, pH 8.0, 3 mM EDTA, 0.1% Tween™-20) and immediately pipetted directly into each capture column.

3. The capture columns were incubated at 37° C. (in an incubator or heat block) for 5 min.

4. The hybridization solutions were recovered by spinning the columns at approx. 7000 RCF for 60 sec.

5. The second set of capture columns was fitted into collection tubes and 40 $\mu$l of hybridization mixture recovered from each of the first columns was pipetted directly into second capture columns. The second capture columns were incubated at 37° C. for 5 min. and the hybridization solution removed by spinning the columns at approx. 7000 RCF for 60 sec. At this point, both forward and reverse reactions have been captured and separated.

6. All capture columns were then fitted into 2 ml wash tubes and washed with 300 $\mu$l 1× TET buffer followed by 300 $\mu$l 70% aqueous isopropanol. Each wash was removed by spinning the columns at 7000 RCF for 60 sec. and discarded.

7. The capture columns were then fitted into clean collection tubes (1.5 ml) and 60 $\mu$l 70% $NH_4OH$ was pipetted into each column to denature the hybridized complexes. This solution was removed by spinning the columns at approx. 7000 RCF for 60 sec., and the eluates were dried in a speed-vacuum centrifuge.

8. For sequencing, the dried pellets from each column were resuspended in 3 $\mu$l of gel loading buffer (5:1 deionized formamide: 50 mM EDTA) and incubated at 98° C. for 2 min. to denature. 1.0–1.5 $\mu$l was loaded onto a 377 ABI Prism™ DNA Sequencer (P.E. Applied Biosystems, Foster City, Calif.) and a sequence printout obtained.

7.2 Results

The results of the capture sequencing reactions are illustrated in FIG. 2. The sequence is identical to that obtained using standard dye primer and dye fluorescence sequencing chemistry.

The foregoing written specification is considered to be sufficient to enable one skilled in the art to practice the invention. Various modifications of the above-described modes for carrying out the invention which are obvious to those skilled in the molecular biological, biochemical and related arts are intended to be within the scope of the appended claims.

All cited references are hereby incorporated herein by reference in their entireties.

What is claimed is:

1. A flow-through device for capturing a target nucleic acid comprising a three-dimensional porous substrate composed of a polymeric material selected from the group consisting of polyethylene, polystyrene, polycarbonate and polypropylene and having immobilized thereon about $6 \times 10^{-17}$ to $6 \times 10^{-16}$ nmol/nm² of a capture polynucleotide which is capable of hybridizing to the target nucleic acid, and wherein said porous substrate is about 1 mm to 20 mm thick.

2. The flow-through device of claim 1 in which said porous substrate has an average pore size of about 1 µm to about 250 µm.

3. The flow-through device of claim 1 in which the porous substrate has a porosity in the range of about 25 to 80%.

4. The flow-through device of claim 1 or 6 in which the capture polynucleotide is covalently immobilized on the porous substrate via its 5'- or 3'-terminal residue.

5. The flow-through device of claim 4 further including a linker disposed between the porous substrate and the capture polynucleotide.

6. A flow-through device for capturing a target nucleic acid, comprising a three-dimensional porous substrate composed of a polymeric material selected from the group consisting of polyethylene, polystyrene, polycarbonate and polypropylene and having an average pore size of about 10 µm to about 100 µm and a porosity in the range of about 25 to 80% and having immobilized thereon a capture polynucleotide capable of hybridizing to the target nucleic acid.

7. The flow-through device of claim 6 in which said porous substrate is about 1 mm to 20 mm thick.

8. The flow-through device of claim 6 in which said porous substrate has immobilized thereon about $2 \times 10^{-19}$ to $2 \times 10^{-15}$ nmol/nm² of said capture polynucleotide.

9. The flow-through device of claim 1 or 6 in which said capture polynucleotide is covalently attached to the porous substrate.

10. The flow-through device of claim 1 or 6 in which said capture polynucleotide is covalently attached to the porous substrate via a phosphodiester, phosphorothioate or phosphoramidate linkage.

11. The flow-through device of claim 1 or 6 in which said capture polynucleotide is covalently attached to the porous substrate via a carboxyamide linkage.

12. The flow-through device of claim 1 or 6 in which said capture polynucleotide is covalently attached to the porous substrate via a linker.

13. The flow-through device of claim 1 or 6 in which said porous substrate has a void volume in the range of about 1 µl/cm² to about 100 µl/cm².

14. The flow-through device according to claim 1 or 6 further comprising a housing in which the three-dimensional porous substrate is disposed.

15. The flow-through device of claim 14, in which said housing is selected from the group consisting of a syringe barrel, a pipette, a disposable pipette tip, a chromatography column, a spin column, a microchannel, a capillary and a multi-well plate.

16. A method of capturing a target nucleic acid from a sample, said method comprising flowing a sample containing or suspected of containing a target nucleic acid through a flow-through device according to claim 1 under conditions wherein said target nucleic acid and capture polynucleotide hybridize to one another to form a hybridized complex, thereby capturing the target nucleic acid.

17. A method of capturing a target nucleic acid from a sample, said method comprising flowing a sample containing or suspected of containing a target nucleic acid thorough a flow-through device according to claim 6 under conditions wherein said target nucleic acid and capture polynucleotide hybridize to one another to form a hybridized complex, thereby capturing the target nucleic acid.

18. The method of claim 16 or 17 in which said target nucleic acid is applied to the flow-through device under conditions wherein it hybridizes with said capture polynucleotide in less than one minute.

19. The method of claim 16 in which said porous substrate of said flow-through device has an average pore size of about 1 µm to about 250 µm.

20. The method of claim 17 in which the density or surface concentration of said capture polynucleotide is about $2 \times 10^{-19}$ to $2 \times 10^{-15}$ nmol/nm².

21. The method of claim 16 or 17 in which said capture polynucleotide is covalently attached to the porous substrate of the flow-through device.

22. The method of claims 16 or 17 in which said capture polynucleotide is covalently attached to the porous substrate of the flow-through device via a phosphodiester, phosphorothioate or phosphoramidate linkage.

23. The method of claim 16 or 17 in which said capture polynucleotide is covalently attached to the porous substrate of the flow-through device via a carboxyamide linkage.

24. The method of claim 16 or 17 in which said capture polynucleotide is covalently attached to the porous substrate of the flow-through device via a linker.

25. The method of claim 16 or 17 in which said porous substrate of said flow-through device has a void volume in the range of 0.1 $\mu l/cm^2$ to about 100 $\mu l/cm^2$.

26. The method of claim 16 or 17 which further includes the step of washing said hybridized complex.

27. A method of determining whether a sample contains a target nucleic acid, said method comprising the steps of:
    (a) flowing a sample suspected of containing a target nucleic acid through a flow-through device according to claim 1 or 6 under conditions wherein the target nucleic acid and capture polynucleotide hybridize; and
    (b) detecting the presence of hybrids, wherein a positive detection indicates the presence of the target nucleic acid in the sample.

28. The method of claim 27, in which said target nucleic acid bears a reporter moiety and hybrids are detected by detecting the presence of said reporter moiety.

29. A kit for capturing a target nucleic acid of interest from a sample, comprising:
    a) a flow-through device according to claim 1 or 6; and
    b) a housing into which the flow-through device can be disposed.

30. A kit for capturing a target nucleic acid from a sample comprising:
    a) a flow-through device according to claims 1 or 6; and
    b) a capture polynucleotide capable of being covalently attached to the porous substrate.

31. The kit of claim 30 further including a linker capable of being covalently attached to the porous substrate and the capture polynucleotide.

32. The kit of claim 30 or 31 in which the porous substrate is activated with about $6 \times 10^{-17}$ to $9 \times 10^{15}$ nmol/nm$^2$ of a reactive group.

33. A kit for capturing a target nucleic acid from a sample comprising:
    a) a flow-through device according to claims 1 or 6; and
    b) means for generating a capture polynucleotide which is capable of hybridizing to the target nucleic acid and which is capable of being covalently attached to the porous substrate.

34. A flow-through device for capturing a target nucleic acid, comprising a three-dimensional porous substrate composed of a polymeric material selected from the group consisting of polyethylene, polystyrene, polycarbonate and polypropylene and having a porosity in the range of about 25 to 80% and having immobilized thereon a capture polynucleotide capable of hybridizing to the target nucleic acid.

35. A flow-through device for capturing a target nucleic acid, comprising a three-dimensional porous substrate composed of a polymeric material selected from the group consisting of glass, polyethylene, polystyrene, polycarbonate and polypropylene and having an average pore size of about 10 $\mu$m to about 100 $\mu$m and a porosity in the range of about 25 to 80% and having immobilized thereon about $6 \times 10^{-17}$ to $6 \times 10^{-16}$ nmol/nm$^2$ of a capture polynucleotide which is capable of hybridizing to the target nucleic acid.

36. A flow-through device for capturing a target nucleic acid, comprising a three-dimensional porous substrate composed of a polymeric material selected from the group consisting of glass, polyethylene, polystyrene, polycarbonate and polypropylene and having an average pore size of about 10 $\mu$m to about 100 $\mu$m and a porosity in the range of about 25 to 80% and having immobilized thereon a capture polynucleotide capable of hybridizing to the target nucleic acid, wherein said porous substrate is about 1 mm to 20 mm thick.

37. A flow-through device for capturing a target nucleic acid, comprising a three-dimensional porous substrate composed of a polymeric material selected from the group consisting of glass, polyethylene, polystyrene, polycarbonate and polypropylene and having an average pore size of about 10 $\mu$m to about 100 $\mu$m and having immobilized thereon about $6 \times 10^{-17}$ to $6 \times 10^{-16}$ nmol/nm$^2$ of a capture polynucleotide which is capable of hybridizing to the target nucleic acid, wherein said porous substrate is about 1 mm to 20 mm thick.

38. A flow-through device for capturing a target nucleic acid, comprising a three-dimensional porous substrate composed of a polymeric material selected from the group consisting of glass, polyethylene, polystyrene, polycarbonate and polypropylene and having a porosity in the range of about 25 to 80% and having immobilized thereon about $6 \times 10^{-17}$ to $6 \times 10{-16}$ nmol/nm$^2$ of a capture polynucleotide which is capable of hybridizing to the target nucleic acid, wherein said porous substrate is about 1 mm to 20 mm thick.

39. A flow-through device for capturing a target nucleic acid, comprising a three-dimensional porous substrate composed of a polymeric material selected from the group consisting of glass, polyethylene, polystyrene, polycarbonate and polypropylene and having an average pore size of about 1 $\mu$m to about 250 $\mu$m and a porosity in the range of about 25 to 80% and having immobilized thereon about $2 \times 10^{-19}$ to $2 \times 10^{-15}$ nmol/nm$^2$ of a capture polynucleotide which is capable of hybridizing to the target nucleic acid, wherein said porous substrate is about 1 mm to 20 mm thick.

40. The flow-through device of claim 34, 35, 36, 37, 38 or 39 in which said capture polynucleotide is covalently attached to the porous substrate.

41. The flow-through device of claim 34, 35, 36, 37, 38 or 39 in which said porous substrate has a void volume in the range of about 1 $\mu l/cm^2$ to about 100 $\mu l/cm^2$.

42. The flow-through device of claim 34, 35, 36, 37, 38 or 39 in which the capture polynucleotide is covalently immobilized on the porous substrate via its 5'- or 3'-terminal residue.

43. The flow-through device according to claim 34, 35, 36, 37, 38 or 39 further comprising a housing in which the three-dimensional porous substrate is disposed.

44. A method of capturing a target nucleic acid from a sample, said method comprising flowing a sample containing or suspected of containing a target nucleic acid through a flow-through device according to claim 34, 35, 36, 37, 38 or 39 under conditions wherein said target nucleic acid and capture polynucleotide hybridize to one another to form a hybridized complex, thereby capturing the target nucleic acid.

45. The method of claim 44 in which said target nucleic acid is applied to the flow-through device under conditions wherein it hybridizes with said capture polynucleotide in less than one minute.

* * * * *